United States Patent
Roettger et al.

(10) Patent No.: US 11,634,372 B2
(45) Date of Patent: Apr. 25, 2023

(54) METHOD FOR THE ENERGY-EFFICIENT PRODUCTION OF SODIUM AND POTASSIUM ALCOHOLATES

(71) Applicant: Evonik Functional Solutions GmbH, Niederkassel (DE)

(72) Inventors: Dirk Roettger, Cologne (DE); Sebastian Reimann, Wesseling (DE); Manfred Neumann, Marl (DE); Moritz Schröder, Muenster (DE); Philip Zitzewitz, Haltern am See (DE); Niklas Paul, Marl (DE); Armin Matthias Rix, Marl (DE)

(73) Assignee: Evonik Functional Solutions GmbH, Niederkassel (DE)

( * ) Notice: Subject to any disclaimer, the term of this patent is extended or adjusted under 35 U.S.C. 154(b) by 0 days.

(21) Appl. No.: 17/759,116

(22) PCT Filed: Nov. 30, 2020

(86) PCT No.: PCT/EP2020/083892
§ 371 (c)(1),
(2) Date: Jul. 20, 2022

(87) PCT Pub. No.: WO2021/148175
PCT Pub. Date: Jul. 29, 2021

(65) Prior Publication Data
US 2023/0047252 A1    Feb. 16, 2023

(30) Foreign Application Priority Data

Jan. 23, 2020 (EP) .................................. 20153356

(51) Int. Cl.
*C07C 29/70* (2006.01)
*C07C 31/30* (2006.01)

(52) U.S. Cl.
CPC ............ *C07C 29/705* (2013.01); *C07C 31/30* (2013.01)

(58) Field of Classification Search
CPC ............................ C07C 29/705; C07C 31/30
See application file for complete search history.

(56) References Cited

U.S. PATENT DOCUMENTS

| 1,910,331 | A | 5/1933 | Halbig |
| 2,295,256 | A | 9/1942 | Brugma |

(Continued)

FOREIGN PATENT DOCUMENTS

| CN | 208632416 U | 3/2019 |
| DE | 968 903 | 4/1958 |

(Continued)

OTHER PUBLICATIONS

Dejanović et al., "Dividing wall column—A breakthrough towards sustainable distilling", Chemical Engineering and Processing, vol. 29, 2010, pp. 559-580.

(Continued)

*Primary Examiner* — Yate' K Cutliff
(74) *Attorney, Agent, or Firm* — Grüneberg and Myers PLLC (57) ABSTRACT

A method can be used for producing alkali metal alcoholates in counter flow by reactive rectification. The alkali metal is selected from sodium and potassium. In a first part of the method, the alcohol is converted in counter flow with the respective alkali metal hydroxide. In a second part of the method, the mixture of alcohol and water obtained is separated in a rectification column, and the alcoholic vapour arising is condensed, as a result of which the temperature thereof increases. The energy dissipated during cooling of the condensed vapour is then used in the first part of the (Continued)

method. This permits an energy-efficient production of the alkali metal alcoholates concerned.

14 Claims, 2 Drawing Sheets

(56) References Cited

U.S. PATENT DOCUMENTS

| | | | |
|---|---|---|---|
| 2,877,274 | A | 3/1959 | Kramis |
| 4,566,947 | A | 1/1986 | Tsuruta |
| 4,895,989 | A | 1/1990 | Sander et al. |
| 7,273,956 | B2 | 9/2007 | Ruwwe et al. |
| 7,847,133 | B2 | 12/2010 | Ruwwe et al. |
| 2002/0183566 | A1 | 12/2002 | Guth et al. |
| 2004/0097759 | A1 | 5/2004 | Ruwwe et al. |
| 2008/0296786 | A1 | 12/2008 | Ruwwe et al. |
| 2011/0313207 | A1* | 12/2011 | Kaibel .................... C07C 29/70 203/18 |
| 2013/0023683 | A1 | 1/2013 | Ruwwe et al. |

FOREIGN PATENT DOCUMENTS

| | | |
|---|---|---|
| EP | 0 122 367 | 10/1984 |
| EP | 0 126 288 | 11/1984 |
| EP | 3 184 502 | 6/2017 |
| GB | 377 631 | 7/1932 |
| GB | 737 453 | 9/1955 |
| WO | 2010/097318 | 9/2010 |
| WO | 2021/148174 | 7/2021 |
| WO | 2021/148175 | 7/2021 |

OTHER PUBLICATIONS

Hossain et al., "Effects of catalyst types and concentrations on biodiesel production from waste soybean oil biomass as renewable energy and environmental recycling process", Australian Journal of Crop Science, vol. 4, No. 7, 2010, pp. 550-555.
International Search Report dated Feb. 11, 2021 in PCT/EP2020/083892, with English translation, 5 pages.
Written Opinion dated Feb. 11, 2021 in PCT/EP2020/083892, with English translation, 9 pages.
U.S. Pat. No. 7,273,956, Sep. 25, 2007, 2004/0097759, Ruwwe et al.
U.S. Appl. No. 60/935,715, filed Aug. 28, 2007, Ruwwe et al.
U.S. Pat. 7,847,133, Dec. 7, 2010, 2008/0296786, Ruwwe et al.
U.S. Appl. No. 13/552,707, filed Jul. 19, 2012, 2013/0023683, Ruwwe et al.
U.S. Appl. No. 17/659,086, filed Apr. 13, 2022, Roettger et al.

* cited by examiner

METHOD FOR THE ENERGY-EFFICIENT PRODUCTION OF SODIUM AND POTASSIUM ALCOHOLATES

CROSS-REFERENCE TO RELATED APPLICATIONS

This application is the National Stage entry under § 371 of International Application No. PCT/EP2020/083892, filed on Nov. 30, 2020, and which claims the benefit of priority to European Application No. 20153356.9, filed on Jan. 23, 2020. The content of each of these applications is hereby incorporated by reference in its entirety.

BACKGROUND OF THE INVENTION

Field of the Invention

The present invention relates to a process for producing alkali metal alkoxides in countercurrent by reactive rectification, wherein the alkali metal is selected from sodium and potassium. In a first step the alcohol is reacted in countercurrent with the relevant alkali metal hydroxide. In a second step the obtained mixture of alcohol and water is separated in a rectification column and the generated alcoholic vapours are compressed to increase their temperature. In contrast to conventional processes the energy removed upon cooling of the compressed vapours is utilized by employing it in the first step of the process according to the invention. This allows energy-efficient production of the relevant alkali metal alkoxides.

Description of Related Art

The production of alkali metal alkoxides is an important industrial process.

Alkali metal alkoxides are used as strong bases in the synthesis of numerous chemicals, for example in the production of pharmaceutical or agrochemical active ingredients. Alkali metal alkoxides are also used as catalysts in transesterification and amidation reactions.

Alkali metal alkoxides (MOR) are produced by reactive distillation of alkali metal hydroxides (MOH) and alcohols (ROH) in a countercurrent distillation column, wherein the reaction water formed according to the following reaction <1> is removed with the distillate.

Such a process principle is described, for example, in U.S. Pat. No. 2,877,274 A, wherein aqueous alkali metal hydroxide solution and gaseous methanol are passed into a rectification column in countercurrent. This process is described again in principally unchanged form in WO 01/42178 A1.

Similar processes, which, however, additionally employ an entraining agent such as benzene, are described in GB 377,631 A and U.S. Pat. No. 1,910,331 A. This entraining agent is used to separate water and the water-soluble alcohol. In both patents the condensate is subjected to a phase separation to separate off the reaction water.

Accordingly, DE 96 89 03 C describes a process for continuous production of alkali metal alkoxides in a reaction column, wherein the water-alcohol mixture withdrawn at the top of the column is condensed and then subjected to a phase separation. The aqueous phase is discarded and the alcoholic phase is returned to the top of the column together with the fresh alcohol. EP 0 299 577 A2 describes a similar process, wherein the water in the condensate is separated off with the aid of a membrane.

The industrially important alkali metal alkoxides are those of sodium and potassium, especially the methoxides and ethoxides. Their synthesis is frequently described in the prior art, for example in EP 1 997 794 A1.

The syntheses of alkali metal alkoxides by reactive rectification described in the prior art typically afford vapours comprising the employed alcohol and water. It is advantageous to for economic reasons to reuse the alcohol comprised in the vapours as a reactant in the reactive distillation. The vapours are therefore typically supplied to a rectification column and the alcohol present therein separated (described for example in GB 737 453 A and U.S. Pat. No. 4,568,947 A). The thus recovered alcohol is then supplied to the reactive distillation as a reactant for example. Alternatively or in addition a portion of the alcohol vapour may be utilized for heating the rectification column (described in WO 2010/097318 A1). However, this requires that the vapour be compressed to achieve the temperature level required for heating the rectification column. Especially a multistage compression of the vapour is thermodynamically advantageous. The vapour is cooled between the compression stages here. The intermediate cooling also ensures that the maximum allowable temperature of the compressor is not exceeded.

The disadvantage of this cooling performed in the customary processes is that the energy thus withdrawn dissipates without being utilized.

There is therefore a need for improved processes for producing alkoxides of sodium and potassium by reactive distillation. These shall avoid the abovementioned disadvantages and especially allow energy-efficient utilization of the heat generated during compression and cooling of the vapours.

BRIEF SUMMARY OF THE INVENTION

The present invention accordingly provides a process for producing at least one alkali metal alkoxide of formula $M_A OR$, wherein R is a $C_1$ to $C_6$ hydrocarbon radical, preferably methyl, and wherein $M_A$ is a metal selected from sodium, potassium, preferably sodium, wherein:

(a1) a reactant stream $S_{AE1}$ comprising ROH is reacted with a reactant stream $S_{AE2}$ comprising $M_A OH$ in countercurrent in a reactive rectification column $RR_A$ to afford a crude product $RP_A$ comprising $M_A OR$, water, ROH, $M_A OH$, wherein a bottoms product stream $S_{AP}$ comprising ROH and $M_A OR$ is withdrawn at the lower end of $RR_A$ and a vapour stream $S_{AB}$ comprising water and ROH is withdrawn at the upper end of $RR_A$, (a2) and optionally, simultaneously with and spatially separate from step (a1), a reactant stream $S_{BE1}$ comprising ROH is reacted with a reactant stream $S_{BE2}$ comprising $M_B OH$ in countercurrent in a reactive rectification column $RR_B$ to afford a crude product $RP_B$ comprising $M_B OR$, water, ROH, $M_B OH$, wherein $M_B$ is a metal selected from sodium, potassium, preferably potassium, wherein a bottoms product stream $S_{BP}$ comprising ROH and $M_B OR$ is withdrawn at the lower end of $RR_B$ and a vapour stream $S_{BB}$ comprising water and ROH is withdrawn at the upper end of $RR_B$, (b) the vapour stream $S_{AB}$ and, when step (a2) is performed, the vapour stream $S_{BB}$, in admixture with $S_{AB}$ or separately from $S_{AB}$, preferably in admixture with $S_{AB}$, is passed into a rectification column $RD_A$ and in $RD_A$ is separated into an ROH-comprising vapour stream $S_{B2}$ having a pressure $p_{B2}$ and a temperature $T_{B2}$ at the top of $RD_A$ and a water stream $S_W$ at the bottom of $RD_A$, (c) at least a portion of the vapour stream $S_{B2}$ is compressed to obtain a vapour stream $S_{B3}$ compressed with respect to $S_{B2}$ having a pressure $p_{B3} > p_{B2}$ and a temperature $T_{B3} > T_{B2}$, (d) energy from $S_{B3}$ is transferred to at least one of $RP_A$, $S_{AE1}$, $S_{AE2}$, $S_{AP}$, $S_{AB}$ and, when step (a2) is performed, alternatively or additionally, preferably additionally, transferred to at least one of $RP_B$, $S_{BE1}$, $S_{BE2}$, $S_{BP}$, $S_{BB}$, to obtain a vapour stream $S_{B4}$ having a lower energy content than $S_{B3}$.

In a preferred embodiment of the process according to the invention the vapour stream $S_{B4}$ is used for heating the rectification column $RD_A$ and/or, preferably and, recycled into said column in a step (e).

DETAILED DESCRIPTION OF THE INVENTION 4.1 Step (a1) of the Process According to the Invention In step (a1) of the process according to the invention a reactant stream $S_{AE1}$ comprising ROH is reacted with a reactant stream $S_{AE2}$ comprising $M_A$OH in countercurrent in a reactive distillation column $RR_A$ to afford a crude product $RP_A$ comprising $M_A$OR, water, ROH, $M_A$OH, According to the invention a "reactive rectification column" is to be understood as meaning a rectification column in which, at least in some parts, the reactions according to step (a1) or step (a2) of the process according to the invention are carried out. It may also be abbreviated to "reaction column".

In step (a1) of the process according to the invention a bottoms product stream $S_{AP}$ comprising ROH and $M_A$OR is withdrawn at the lower end of $RR_A$. A vapour stream $S_{AB}$ comprising water and ROH is withdrawn at the upper end of $RR_A$.

In the process according to the invention R is a $C_1$ to $C_6$ hydrocarbon radical, preferably selected from the group consisting of methyl, ethyl, n-propyl, iso-propyl, n-butyl, sec-butyl, iso-butyl, tart-butyl, isomers of pentyl such as for example n-pentyl, more preferably selected from the group consisting of methyl, ethyl, n-propyl, iso-propyl, yet more preferably selected from the group consisting of methyl and ethyl. R is particularly preferably methyl and ROH is accordingly methanol.

$M_A$ is selected from sodium, potassium, preferably sodium.

The reactant stream $S_{AE1}$ comprises ROH. In a preferred embodiment the mass fraction of ROH in $S_{AE1}$ is ≥95% by weight, yet more preferably ≥99% by weight, wherein $S_{AE1}$ otherwise comprises especially water.

The alcohol ROH employed in step (a1) of the process according to the invention as reactant stream $S_{AE1}$ may also be commercially available alcohol having an alcohol mass fraction of more than 99.8% by weight and a mass fraction or water of up to 0.2% by weight.

The reactant stream $S_{AE1}$ is preferably added in vaporous form.

The reactant stream $S_{AE2}$ comprises $M_A$OH. In a preferred embodiment $S_{AE2}$ comprises not only $M_A$OH but also at least one further compound selected from water, ROH. It is yet more preferable when $S_{AE2}$ comprises water in addition to $M_A$OH, thus rendering $S_{AE2}$ an aqueous solution of $M_A$OH.

When the reactant stream $S_{AE2}$ comprises $M_A$OH and water the mass fraction of $M_A$OH based on the total weight of the aqueous solution forming $S_{AE2}$ is especially in the range from 10% to 55% by weight, preferably from 15% to 54% by weight, more preferably from 30% to 53% by weight and particularly preferably from 45% to 52% by weight. It is most preferable when the proportion of $M_A$OH in the aqueous solution is 50% by weight.

When the reactant stream $S_{AE2}$ comprises $M_A$OH and ROH the mass fraction of $M_A$OH in ROH based on the total weight of the solution forming SAE is especially in the range from 10% to 55% by weight, preferably from 15% to 54% by weight, more preferably from 30% to 53% by weight and particularly preferably from 45% to 52% by weight.

In the particular case in which the reactant stream SA comprises both water and ROH in addition to $M_A$OH it is particularly preferable when the mass fraction of $M_A$OH in ROH and water based on the total weight of the solution forming $S_{AE2}$ is especially in the range from 10% to 55% by weight, preferably from 15% to 54% by weight, more preferably from 30% to 53% by weight and particularly preferably from 45% to 52% by weight.

Step (a1) of the process according to the invention is performed in a reactive rectification column (or "reaction column") $RR_A$.

Step (a2) of the process according to the invention is performed in a reactive rectification column (or "reaction column") $RR_B$.

The reaction column $RR_A/RR_B$ preferably contains internals. Suitable internals are, for example, trays, structured packings or unstructured packings. When the reaction column $RR_A/RR_B$ contains trays, suitable trays include bubble cap trays, valve trays, tunnel cap trays, Thormann trays, cross-slit bubble cap trays or sieve trays. When the reaction column $RR_A/RR_B$ contains trays it is preferable to select trays where at most 5% by weight, preferably less than 1% by weight, of the liquid trickles through the respective trays. The constructional measures required to minimize trickle-through of the liquid are familiar to those skilled in the art. In the case of valve trays, particularly tightly closing valve designs are selected for example. Reducing the number of valves also makes it possible to increase the vapour velocity in the tray openings to double the value typically established. When using sieve trays it is particularly advantageous to reduce the diameter of the tray openings while maintaining or even increasing the number of openings.

When using structured or unstructured packings, structured packings are preferred in terms of uniform distribution of the liquid. In this embodiment it is further provided that in all parts of the column cross section corresponding to more than 2% of the total column cross section the average ratio of liquid stream to vapour stream must not be exceeded by more than 15%, preferably by more than 3%, in respect of the liquid. This minimized liquid amount makes it possible for the capillary effect at the wire meshes to eliminate local peaks of liquid sprinkling density.

For columns comprising unstructured packings, especially comprising random packings, and for columns comprising structured packings the desired characteristics of the liquid distribution may be achieved when the liquid sprinkling density in the edge region of the column cross section adjacent to the column shell, corresponding to about 2% to 5% of the total column cross section, is reduced compared to the other cross sectional regions by up to 100%, preferably by 5% to 15%. This is easily achievable for example through specific distribution of the drip points of the liquid distributors or their bores.

The process according to the invention may be carried out either continuously or discontinuously. It is preferably carried out continuously.

According to the invention "reaction of a reactant stream $S_{AE1}$ comprising ROH with a reactant stream $S_{AE2}$ comprising $M_AOH$ in countercurrent" is especially achieved as a result of the feed point for at least a portion of the reactant stream SAE, comprising ROH in step (a1) being arranged on the reaction column $RR_A$ below the feed point for the reactant stream $S_{AE2}$ comprising $M_AOH$.

The reaction column $RR_A$ preferably comprises at least 2, in particular 15 to 40, theoretical trays between the feed point of the reactant stream $S_{AE1}$ and the feed point of the reactant stream $S_{AE2}$.

The reaction column $RR_A$ is preferably operated as a pure stripping column. Accordingly the reactant stream $S_{AE1}$ comprising ROH is especially supplied in vaporous form in the lower region of the reaction column $RR_A$. Step (a1) of the process according to the invention also comprises the case where a portion of the reactant stream $S_{AE1}$ comprising ROH is added in vaporous form below the feed point of the reactant stream $S_{AE2}$ comprising aqueous sodium hydroxide solution $M_AOH$ but nevertheless at the upper end or In the region of the upper end of the reaction column $RR_A$. This makes it possible to reduce the dimensions of the lower region of the reaction column $RR_A$. When a portion of the reactant stream $S_{AE1}$ comprising ROH, in particular methanol, is added especially in vaporous form at the upper end or in the region of the upper end of the reaction column $RR_A$ only a fraction of 10% to 70% by weight, preferably of 30% to 50% by weight, (in each case based on the total amount of the alcohol ROH employed in step (a1)) is introduced at the lower end of the reaction column $RR_A$ and the remaining fraction is added in vaporous form in a single stream or divided into a plurality of substreams preferably 1 to 10 theoretical trays, particularly preferably 1 to 3 theoretical trays, below the feed point or the reactant stream $S_{AE2}$ comprising $M_AOH$.

In the reaction column $RR_A$ the reactant stream $S_{AE1}$ comprising ROH is then reacted with the reactant stream $S_{AE2}$ comprising $M_AOH$ according to the reaction <1> described hereinabove to afford $M_AOR$ and $H_2O$, wherein these products are present in admixture with the reactants ROH und $M_AOH$ since an equilibrium reaction is concerned. Accordingly a crude product $RP_A$ which contains not only the products $M_AOR$ and water but also ROH and $M_AOH$ is obtained in the reaction column $RR_a$ in step (a1) of the process according to the invention.

The bottoms product stream $S_{AP}$ comprising ROH and $M_AOR$ is obtained and then withdrawn at the lower end of $RR_A$.

A water-containing alcohol stream, described hereinabove as "vapour stream $S_{AB}$ comprising water and ROH", is withdrawn at the upper end of $RR_A$, preferably at the column top of $RR_A$.

This vapour stream $S_{AB}$ comprising water and ROH is supplied to step (b) of the process according to the invention. As part of at least one of the streams $S_{B2}$, $S_{B3}$, $S_{B4}$ a portion of the alcohol obtained in the distillation in step (b) may be supplied to the reaction column $RR_A$ as reactant stream $S_{AE1}$.

The amount of the alcohol ROH comprised by the reactant stream $S_{AE1}$ is preferably chosen such that said alcohol also serves as a solvent for the alkali metal alkoxide $M_AOR$ obtained in the bottoms product stream $S_{AP}$. The amount of the alcohol ROH in the reactant stream $S_{AE1}$ is preferably chosen to achieve in the bottom of reaction column the desired concentration of the alkali metal alkoxide solution which is withdrawn as a bottoms product stream $S_{AP}$ comprising ROH and $M_AOR$.

In a preferred embodiment of the process according to the invention, and especially in the cases where $S_{AE2}$ contains water in addition to $M_AOH$, the ratio of the total weight (masses; units: kg) of alcohol employed in step (a1) as reactant stream $S_{AE1}$ ROH to the total weight (masses; unit: kg) of $M_AOH$ employed in step (a1) as reactant stream $S_{AE2}$ is 4:1 to 50:1, more preferably 9:1 to 48:1, yet more preferably 13:1 to 35:1, yet still more preferably 22:1 to 30:1.

The reaction column $RR_A$ is operated with or without, preferably without, reflux.

"Without reflux" is to be understood as meaning that the vapour stream $S_{AB}$ withdrawn at the upper end of $RR_A$ comprising water and ROH is completely supplied to the rectification column $RD_A$ according to step (b). The vapour stream $S_{AB}$ comprising water and ROH is preferably supplied to the rectification column $RD_A$ in vaporous form.

"With reflux" is to be understood as meaning that the vapour stream $S_{AB}$ withdrawn at the upper end of the respective column, reaction column $RR_A$ in step (a1), comprising water and ROH is not completely discharged, i.e. is not completely supplied to the rectification column $RD_A$ in step (b), but rather is at least partially, preferably partially, supplied to the respective column, reaction column $RR_A$ in step (a1), as reflux. In the cases where such a reflux is established the reflux ratio is preferably 0.05 to 0.99, more preferably 0.1 to 0.9, yet more preferably 0.11 to 0.34, particularly preferably 0.14 to 0.27 and very particularly preferably 0.17 to 0.24. A reflux may be established by attaching to the top of the respective column, reaction column $RR_A$ in step (a1), a condenser $K_{RRA}$ in which the vapour stream $S_{AB}$ is at least partially condensed and sent back to the respective column, reaction column $RR_A$ in step (a1). Generally and in the context of the present invention a reflux ratio is to be understood as meaning the ratio of the mass flow (kg/h) recycled to the respective column in liquid form (reflux) to the mass flow (kg/h) discharged from the respective column in liquid form (distillate) or gaseous form (vapours).

In the embodiment in which a reflux is established on the reaction column $RR_A$ the $M_AOH$ employed in step (a1) as reactant stream SAE may also be at least partially mixed with the reflux stream and the resulting mixture thus supplied to step (a1).

Step (a1) of the process according to the invention is carried out especially at a temperature in the range of 45° C. to 150° C., preferably 47° C. to 120° C., more preferably 60° C. to 110° C., and at a pressure of 0.5 bar to 40 bar, preferably in the range from 0.75 bar to 5 bar, more preferably in the range from 1 bar to 2 bar, more preferably in the range from 1 bar to 1.5 bar, yet more preferably at ambient pressure (1 bar).

The reaction column $RR_A$ comprises in a preferred embodiment at least one evaporator which is in particular selected from intermediate evaporators $V_{ZA}$ and bottoms evaporators $V_{SA}$. The reaction column $RR_A$ particularly preferably comprises at least one bottoms evaporator $V_{SA}$.

According to the invention "intermediate evaporators" $V_{ZA}$ and $V_{ZB}$ are to be understood as meaning evaporators arranged above the bottom of the respective column, in particular above the bottom of the reaction column $RR_A/RR_B$. They are used in particular to evaporate crude product $RP_A/RP_B$.

According to the invention "intermediate evaporators" $V_{SA}$ and $V_{SB}$ are to be understood as meaning evaporators which heat the bottom of the respective column, in particular above the bottom of the reaction column $RR_A/RR_B$. These evaporate bottoms product stream $S_{AP}/S_{BP}$.

An evaporator is typically arranged outside the respective reaction column or rectification column. The mixture to be evaporated in the evaporator is withdrawn via a takeoff from the column and supplied to the at least one evaporator. In the case of the reaction column $RR_A/RR_B$ intermediate evaporation of the crude product $RP_A/RP_B$ comprises withdrawal thereof and supply thereof to at least one intermediate evaporator $V_{ZA}/V_{ZB}$. The evaporated mixture is recycled back into the respective column optionally with a residual proportion of liquid via a feed. When the evaporator is an intermediate evaporator, i.e. an intermediate evaporator $V_{ZA}/V_{ZB}$ is especially concerned, the takeoff by means of which the respective mixture is withdrawn and supplied to the evaporator is a sidestream takeoff and the feed by means of which the evaporated respective mixture is sent back to the column is a sidestream feed. When the evaporator is a bottoms evaporator, i.e. heats the column bottom. i.e. a bottoms evaporator $V_{SA}/V_{SB}$ is especially concerned, at least a portion of the bottoms takeoff stream, in particular $S_{AP}/S_{BP}$, is supplied to the bottoms evaporator $V_S$, evaporated and recycled back into the respective column in the region of the bottom. However, it is alternatively also possible for example on a suitable tray when using an intermediate evaporator or in the bottom of the respective column to provide tubes which are traversed by the respective compressed vapour stream $S_{B3}$ or a heating medium $W_1$. In this case the evaporation is carried out on the tray or in the bottom of the column. However, it is preferable to arrange the evaporator outside the respective column.

Suitable evaporators employable as intermediate evaporators and bottoms evaporators include for example natural circulation evaporators, forced circulation evaporators, forced circulation evaporators with decompression, steam boilers, falling film evaporators or thin film evaporators. Heat exchangers typically employed for evaporators in the case of natural circulation evaporators and forced circulation evaporators are shell and tube or plate apparatuses. When using a shell and tube exchanger the compressed vapour stream $S_{B3}$/the heating medium $W_1$ may flow through the tubes with the mixture to be evaporated flowing around the tubes or else the compressed vapour stream $S_{B3}$/the heating medium $W_1$ may flow around the tubes with the mixture to be evaporated flowing through the tubes. In the case of a falling film evaporator the mixture to be evaporated is typically added as a thin film on the inside of a tube and the tube is heated externally. In contrast to a falling film evaporator a thin film evaporator additionally comprises a rotor with wipers which distributes the liquid to be evaporated on the inner wall of the tube to form a thin film.

In addition to the recited evaporator types it is also possible to employ any desired further evaporator type known to those skilled in the art and suitable for use on a rectification column.

When the evaporator operated with the compressed vapour stream $S_{B3}$/the heating medium $W_1$ as heating vapour is an intermediate evaporator it is preferable when the intermediate evaporator is arranged in the stripping portion of the reaction column $RR_A$ in the region of the feed point of the reactant stream $S_{AE1}$ or in the case of the reaction column $RR_B$ in the region of the feed point of the reactant stream $S_{BE1}$. This makes it possible to introduce a predominant proportion of the heat energy via the intermediate evaporator. It is thus possible for example to introduce more than 80% of the energy via the intermediate evaporator. According to the invention the intermediate evaporator is preferably arranged and/or configured such that it introduces more than 50%, in particular more than 75%, of the total energy required for the distillation.

When using an intermediate evaporator it is especially advantageous when the intermediate evaporator is arranged such that the reaction column $RR_A/RR_B$ has 1 to 50 theoretical trays below the intermediate evaporator and 1 to 200 theoretical trays above the intermediate evaporator, it is especially preferred when the reaction column $RR_A/RR_B$ has 2 to 10 theoretical trays below the intermediate evaporator and 20 to 50 theoretical trays above the intermediate evaporator.

The sidestream takeoff stream by means of which the crude product $RP_A/RP_B$ is supplied to the intermediate evaporator $V_{ZA}/V_{ZB}$ and the sidestream feed by means of which the evaporated crude product $RP_A/RP_B$ from the intermediate evaporator $V_{ZA}/V_{ZB}$ is sent back to the respective reaction column $RR_A/RR_B$ may be positioned between the same trays of the reaction column. However, it is also possible for the sidestream takeoff and the site stream feed to be at different heights.

In a preferred embodiment when using an intermediate evaporator $RR_A/RR_B$ the diameter of the reaction column $RR_A/RRS$ above the intermediate evaporator $RR_A/RR_B$ is greater than the diameter of the reaction column $RR_A/RR_B$ below the intermediate evaporator $RR_A/RR_B$. This has the advantage of allowing capital expenditure savings.

Such an intermediate evaporator $V_{ZA}$ can convert liquid crude product $RP_A$ present in the reaction column $RR_A$ comprising $M_AOR$, water, ROH, $M_AOH$ into the gaseous state, thus improving the efficiency of the reaction according to step (a1) of the process according to the invention.

By arranging one or more intermediate evaporators $V_{ZA}$ in the upper region of the reaction column $RR_A$ the dimensions in the lower region of the reaction column $RR_A$ can be reduced. In the embodiment having at least one, preferably two or more, intermediate evaporators $V_{ZA}$ it is also possible to introduce substreams of the ROH in liquid form in the upper region of the reaction column $RR_A$.

According to the invention bottoms evaporators are arranged at the bottom of the reaction column $RR_A/RR_B$ and are then referred to as "$V_{SA}$"/"$V_{SB}$". Bottoms product stream $S_{AP}/S_{BP}$ present in the reaction column $RR_A/RR_B$ may be passed into such a bottoms evaporator and ROH at least partially removed therefrom to obtain a bottoms product stream $S_{AP'}$ having an elevated mass fraction of $M_AOR$ compared to $S_{AP}$/to obtain a bottoms product stream $S_{BP'}$ having an elevated mass fraction of $M_BOR$ compared to $S_{BP}$.

In step (a1) of the process according to the invention a bottoms product stream $S_{AP}$ comprising ROH and $M_AOR$ is withdrawn at the lower end of the reaction column $RR_A$.

It is preferable when the reaction column $RR_A$ comprises at least one bottoms evaporator $V_{SA}$ through which the bottoms product stream $S_{AP}$ is then at least partially passed to at least partially remove ROH, thus affording a bottoms product stream $S_{AP}$ having an elevated mass fraction of $M_AOR$ compared to $S_{AP}$. In this further preferred embodiment it is yet more advantageous when in step (d) $S_{B3}$ or $W_1$ is at least partially passed through a bottoms evaporator $V_{SA}$ and the energy from $S_{B3}/W_1$ is transferred to the bottoms product stream $S_{AP}$, especially by utilizing $S_{B3}/W_1$ to heat the evaporator $V_{A1}$. $W_1$ is a heat transfer medium distinct from $RP_A$, $S_{AE1}$, $S_{AE2}$, $S_{AP}$, $S_{AB}$, $RP_B$, $S_{BE1}$, $S_{BE2}$, $S_{BP}$ or $S_{BB}$ which has contacted $S_{B3}$ so that energy is transferred from $S_{B3}$ to the at least one heat transfer medium $W_1$ (see section 4.5).

The mass fraction of $M_AOR$ in the bottoms product stream $S_AP$ is especially elevated compared to the mass fraction of $M_AOR$ in the bottoms product stream $S_{AP}$ by at least 1%, preferably by ≥2%, more preferably by ≥5%, yet more preferably by ≥10%, yet still more preferably by ≥20%, yet still more preferably by ≥30%, yet still more preferably by ≥40%, yet still more preferably by ≥50%, yet still more preferably by ≥100%, yet still more preferably by ≥150%.

It is preferable when $S_{AP}$ or, if at least one bottoms evaporator $V_{SA}$ through which the bottoms product stream $S_{AP}$ is at least partially passed to at least partially remove ROH is used, $S_{AP'}$ has a mass fraction of $M_AOR$ in ROH in the range from 1% to 50% by weight, preferably 5% to 32% by weight, more preferably 15% to 32% by weight, most preferably 30% to 32% by weight, in each case based on the total mass of $S_{AP}$.

The mass fraction of residual water in $S_{AP}/S_{AP'}$ is preferably <1% by weight, preferably <0.1% by weight, more preferably <0.01% by weight, based on the total mass of $S_{AP}$.

The mass fraction of reactant $M_AOH$ in $S_{AP}/S_{AP}$ is preferably <1% by weight, preferably <0.1% by weight, more preferably <0.01% by weight, based on the total mass of $S_{AP}$.

4.2 Step (a2) of the Process According to the Invention (Optional)

According to the invention step (a2) is optionally performed. In optional step (a2) which is carried out simultaneously with and spatially separate from step (a1) of the process according to the invention a reactant stream $S_{BE1}$ comprising ROH is reacted with a reactant stream $S_{BE2}$ comprising $M_BOH$ in countercurrent in a reactive rectification column $RR_B$ to afford a crude product $RP_B$ comprising $M_BOR$, water, ROH, $M_BOH$.

In step (a2) of the process according to the invention a bottoms product stream $S_{BP}$ comprising ROH and $M_BOR$ is withdrawn at the lower end or $RR_B$. A vapour stream $S_{BB}$ comprising water and ROH is withdrawn at the top end of $RR_B$.

$M_A$ is selected from sodium, potassium, preferably potassium.

The reactant stream $S_{BE1}$ comprises ROH. In a preferred embodiment the mass fraction of ROH in $S_{BE1}$ is ≥95% by weight, yet more preferably ≥99% by weight, wherein $S_{BE1}$ otherwise comprises especially water.

The alcohol ROH employed in step (a2) of the process according to the invention as reactant stream $S_{BE1}$ may also be commercially available alcohol having an alcohol mass fraction of more than 99.8% by weight and a mass fraction or water of up to 0.2% by weight.

The reactant stream $S_{BE1}$ is preferably added in vaporous form.

The reactant stream $S_{BE2}$ comprises $M_BOH$. In a preferred embodiment $S_{BE2}$ comprises not only $M_BOH$ but also at least one further compound selected from water, ROH. It is yet more preferable when $S_{BE2}$ comprises water in addition to $M_BOH$, thus rendering $S_{BE2}$ an aqueous solution of $M_BOH$.

When the reactant stream $S_{BE2}$ comprises $M_BOH$ and water the mass fraction of $M_BOH$ based on the total weight of the aqueous solution forming $S_{BE2}$ is especially in the range from 10% to 55% by weight, preferably from 15% to 54% by weight, more preferably from 30% to 53% by weight and particularly preferably from 45% to 52% by weight. It is most preferable when the proportion of $M_BOH$ in the aqueous solution is 50% by weight.

When the reactant stream $S_{BE2}$ comprises $M_BOH$ and ROH the mass fraction of $M_BOH$ in ROH based on the total weight of the solution forming $S_{BE2}$ is especially in the range from 10% to 55% by weight, preferably from 15% to 54% by weight, more preferably from 30% to 53% by weight and particularly preferably from 45% to 52% by weight.

In the particular case in which the reactant stream $S_{BE2}$ comprises both water and ROH in addition to $M_BOH$ it is particularly preferable when the mass fraction of $M_BOH$ in ROH and water based on the total weight of the solution forming $S_{BE2}$ is especially in the range from 10% to 55% by weight, preferably from 15% to 54% by weight, more preferably from 30% to 53% by weight and particularly preferably from 45% to 52% by weight.

Step (a2) of the process according to the invention is performed in a reactive rectification column (or "reaction column") $RR_B$. Preferred embodiments of the reaction column $RR_B$ are described in section 4.1.

According to the invention "reaction of a reactant stream $S_{BE1}$ comprising ROH with a reactant stream $S_{BE2}$ comprising $M_BOH$ in countercurrent" is especially achieved as a result of the feed point for at least a portion of the reactant stream $S_{BE2}$ comprising ROH in step (a2) being arranged below the feed point for the reactant stream $S_{BE2}$ comprising $M_BOH$ on the reaction column $RR_B$.

The reaction column $RR_B$ preferably comprises at least 2, in particular 15 to 40, theoretical trays between the feed point of the reactant stream $S_{BE1}$ and the feed point of the reactant stream $S_{BE2}$.

The reaction column $RR_B$ is preferably operated as a pure stripping column. Accordingly the reactant stream $S_{BE1}$ comprising ROH is especially supplied in vaporous form in the lower region of the reaction column $RR_B$. Step (a2) of the process according to the invention also comprises the case where a portion of the reactant stream $S_{BE1}$ comprising ROH is added in vaporous form below the feed point of the reactant stream $S_{BE2}$ comprising aqueous sodium hydroxide solution $M_BOH$ but nevertheless at the upper end or in the region of the upper end of the reaction column $RR_B$. This makes it possible to reduce the dimensions of the lower region of the reaction column $RR_B$. When a portion of the reactant stream $S_{BE1}$ comprising ROH, in particular methanol, is added especially in vaporous form at the upper end or in the region of the upper end of the reaction column $RR_B$ only a fraction of 10% to 70% by weight, preferably of 30% to 50% by weight, (in each case based on the total amount of the alcohol ROH employed in step (a2)) is introduced at the lower end of the reaction column $RR_B$ and the remaining fraction is added in vaporous form in a single stream or divided into a plurality of substreams preferably 1 to 10 theoretical trays, particularly preferably 1 to 3 theoretical trays, below the feed point of the reactant stream $S_{BE2}$ comprising $M_BOH$.

In the reaction column $RR_B$ the reactant stream $S_{BE1}$ comprising ROH is then reacted with the reactant stream $S_{BE2}$ comprising $M_BOH$ according to the reaction <1> described hereinabove to afford $M_BOR$ and $H_2O$, wherein these products are present in admixture with the reactants ROH and $M_BOH$ since an equilibrium reaction is concerned. Accordingly a crude product RPs which contains not only the products $M_BOR$ and water but also ROH and $M_BOH$ is obtained in the reaction column $RR_B$ in step (a2) of the process according to the invention.

The bottoms product stream $S_{BP}$ comprising ROH and $M_BOR$ is obtained and then withdrawn at the lower end of $RR_B$.

A water-containing alcohol stream, described hereinabove as "vapour stream $S_{BB}$ comprising water and ROH", is withdrawn at the upper end of $RR_B$, preferably at the column top of $RR_B$.

This vapour stream $S_{BB}$ comprising water and ROH is supplied to step (b) of the process according to the invention. Said stream is mixed with $S_{AB}$ before being supplied to step (b) of the process according to the invention or is not, i.e. is supplied to step (b) of the process according to the invention separately from $S_{AB}$. It is preferable when the vapour stream $S_{BB}$ is mixed with $S_{AB}$ and then the mixture supplied to step (b) of the process according to the invention. As part of at least one of the streams $S_{B2}$, $S_{B3}$, $S_{B4}$ a portion of the alcohol obtained in the distillation in step (b) may be supplied to the reaction column $RR_B$ as reactant stream $S_{BE1}$.

The amount of the alcohol ROH comprised by the reactant stream $S_{BE1}$ is preferably chosen such that said alcohol also serves as a solvent for the alkali metal alkoxide $M_BOR$ obtained in the bottoms product stream $S_{BP}$. The amount of the alcohol ROH in the reactant stream $S_{BE1}$ is preferably chosen to achieve in the bottom of reaction column the desired concentration of the alkali metal alkoxide solution which is withdrawn as a bottoms product stream $S_{BP}$ comprising ROH and $M_BOR$.

In a preferred embodiment of the process according to the invention, and especially in the cases where $S_{BE2}$ contains water in addition to $M_BOH$, the ratio of the total weight (masses; units: kg) of alcohol employed in step (a2) as reactant stream $S_{BE1}$ ROH to the total weight (masses; unit: kg) of $M_BOH$ employed in step (a2) as reactant stream $S_{BE2}$ is 4:1 to 50:1, more preferably from 9:1 to 48:1, yet more preferably from 13:1 to 35:1, yet still more preferably 22:1 to 30:1.

The reaction column $RR_B$ is operated with or without, preferably without, reflux.

"Without reflux" is to be understood as meaning that the vapour stream $S_{BB}$ withdrawn at the upper end of $RR_B$ comprising water and ROH is completely supplied to the rectification column $RD_A$ according to step (b). The vapour stream $S_{BB}$ comprising water and ROH is preferably supplied to the rectification column $RD_A$ in vaporous form.

"Ith reflux" is to be understood as meaning that the vapour stream $S_{BB}$ withdrawn at the upper end of the respective column, reaction column $RR_B$ in step (a2), comprising water and ROH is not completely discharged, i.e. is not completely supplied to the rectification column $RD_A$ in step (b), but rather is at least partially, preferably partially, sent back to the respective column, reaction column $RR_B$ in step (a2), as reflux. In the cases where such a reflux is established the reflux ratio is preferably 0.05 to 0.99, more preferably 0.1 to 0.9, yet more preferably 0.11 to 0.34, particularly preferably 0.14 to 0.27 and very particularly preferably 0.17 to 0.24. A reflux may be established by attaching at the top of the respective column, reaction column $RR_B$ in step (a2), a condenser $K_{RRB}$ In which the vapour stream $S_{BB}$ is at least partially condensed and sent back to the respective column, reaction column $RR_B$ in step (a2).

In the embodiment in which a reflux is established for the reaction column $RR_B$ the $M_BOH$ employed in step (a2) as reactant stream $S_{BE2}$ may also be at least partially mixed with the reflux stream and the resulting mixture thus supplied to step (a2).

Step (a2) of the process according to the invention is carried out especially at a temperature in the range of 45° C. to 150° C., preferably 47° C. to 120° C., more preferably 80° C. to 110° C., and at a pressure of 0.5 bar to 40 bar, preferably in the range from 0.75 bar to 5 bar, more preferably in the range from 1 bar to 2 bar, more preferably in the range from 1 bar to 1.5 bar, yet more preferably at ambient pressure (1 bar).

The reaction column $RR_B$ comprises in a preferred embodiment at least one evaporator which is in particular selected from intermediate evaporators $V_{ZB}$ and bottoms evaporators $V_{SB}$. The reaction column $RR_B$ particularly preferably comprises at least one bottoms evaporator $V_{SB}$.

Such an intermediate evaporator $V_{ZB}$ can convert liquid crude product $RP_B$ present in the reaction column $RR_B$ comprising $M_BOR$, water, ROH, $M_BOH$ into the gaseous state, thus improving the efficiency of the reaction according to step (a2) of the process according to the invention.

By arranging one or more intermediate evaporators $V_{ZB}$ in the upper region of the reaction column $RR_B$ the dimensions in the lower region of the reaction column $RR_B$ can be reduced. In the embodiment having at least one, preferably two or more, intermediate evaporators $V_{ZB}$ it is also possible to introduce substreams of the ROH in liquid form in the upper region of the reaction column $RR_B$.

In step (a2) of the process according to the invention a bottoms product stream $S_{SB}$ comprising ROH and $M_BOR$ is withdrawn at the lower end of the reaction column $RR_B$.

It is preferable when the reaction column $RR_B$ comprises at least one bottoms evaporator $V_{SB}$ through which the bottoms product stream $S_{SB}$ is then at least partially passed to at least partially remove ROH, thus affording a bottoms product stream $S_{BP'}$ having an elevated mass fraction of $M_BOR$ compared to $S_{BP}$. In this further preferred embodiment it is yet more advantageous when in step (d) $S_{B3}$ or $W_1$ is at least partially passed through a bottoms evaporator $V_{SB}$ and the energy from $S_{B3}/W_1$ is transferred to the bottoms product stream $S_{SB}$, especially by utilizing SUM/W to heat the evaporator $V_{B1}$.

The mass fraction of $M_BOR$ in the bottoms product stream $S_{BP'}$ is especially elevated compared to the mass fraction of $M_BOR$ in the bottoms product stream $S_{BP}$ by at least 1%, preferably by ≥2%, more preferably by ≥5%, yet more preferably by ≥10%, yet still more preferably by ≥20%, yet still more preferably by ≥30%, yet still more preferably by ≥40%, yet still more preferably by ≥50%, yet still more preferably by ≥100%, yet still more preferably by ≥150%.

It is preferable when $S_{BP}$ or, if at least one bottoms evaporator $V_{SB}$ through which the bottoms product stream $S_{BP}$ is at least partially passed to at least partially remove ROH is used, $S_{BP'}$ has a mass fraction of $M_BOR$ in ROH in the range from 1% to 50% by weight, preferably 5% to 32% by weight, more preferably 15% to 32% by weight, most preferably 30% to 32% by weight, in each case based on the total mass of $S_{BP'}$.

The mass fraction of residual water in $S_{SB}/S_{BP'}$ is preferably <1% by weight, preferably <0.1% by weight, more preferably <0.01% by weight, based on the total mass of $S_{BP'}$.

The mass fraction of reactant $M_BOH$ in $S_{SB}/S_{BP'}$ is preferably <1% by weight, preferably <0.1% by weight, more preferably <0.01% by weight, based on the total mass of $S_{BP'}$.

In the embodiments of the present process in which step (a2) is also performed it is preferable when the bottoms product stream $S_{AP}$ is at least partially passed through a bottoms evaporator $V_{SA}$ and ROH is at least partially removed from $S_{AP}$ to afford a bottoms product stream $S_{AP'}$ having an elevated mass fraction of $M_AOR$ compared to $S_{AP}$ and/or, preferably and, the bottoms product stream $S_{BP}$ is at least partially passed through a bottoms evaporator $V_{SB}$ and ROH is at least partially removed from $S_{BP}$ to afford a bottoms product stream $S_{BP'}$ having an elevated mass fraction of $M_BOR$ compared to $S_{BP}$. In this further preferred embodiment it is yet more preferable when in step (d) the energy from $S_{B3}$ is transferred to the bottoms product stream $S_{AP}$ and/or, preferably and, the bottoms product stream $S_{BP'}$, in particular utilized in $S_{B3}$ for heating the bottoms evaporator $V_{SA}$ and/or, preferably and, the bottoms evaporator $V_{SB}$. This utilization of the energy from $S_{B3}$ may be effected directly or indirectly.

In the embodiments of the present invention in which it is carried out step (a2) of the process according to the invention is performed simultaneously with and spatially separate from step (a1). Spatial separation is ensured by performing steps (a1) and (a2) in the two reaction columns $RR_A$ and $RR_B$.

In an advantageous embodiment of the invention the reaction columns $RR_A$ and $RR_B$ are accommodated in one column shell, wherein the column is at least partially subdivided by at least one dividing wall. According to the invention such a column comprising at least one dividing wall is referred to as a "TRD". Such dividing wall columns are familiar to those skilled in the art and described for example in U.S. Pat. No. 2,295,258, EP 0 122 387 A2, EP 0 126 288 A2, WO 2010/097318 A1 sowie von I. Dejanović, L j. Matijašević, Ž. Olujić, *Chemical Engineering and Processing* 2010, 49, 559-580. In the dividing wall columns suitable for the process according to the invention the dividing walls preferably extend to the floor and, in particular, preferably span at least a quarter, more preferably at least a third, yet more preferably at least half, yet more preferably at least two thirds, yet still more preferably at least three quarters, of the column by height They divide the columns into at least two reaction spaces in which spatially separate reactions may be carried out. The reaction spaces provided by the at least one dividing wall may be of identical or different sizes.

In this embodiment the bottoms product streams $S_{AP}$ and $S_{BP}$ may be separately withdrawn in the respective regions separated by the dividing wall and preferably passed through the bottoms evaporator $V_{SA}/V_{SB}$ attached for each reaction space formed by the at least one reaction wall in which ROH is at least partially removed from $S_{AP}/S_{BP}$ to afford $S_{AP'}/S_{BP'}$.

4.3 Step (b) of the Process According to the Invention

In step (b) of the process according to the invention the vapour stream $S_{AB}$ is passed into a rectification column $RD_A$ and in $RD_A$ separated into an ROH-comprising vapour stream $S_{B2}$ having a pressure $p_{B2}$ and a temperature $T_{B2}$ at the top of $RD_A$ and a water stream $S_W$ at the bottom of $RD_A$.

In the optional embodiment of the process according to the invention in which step (a2) is performed the vapour stream $S_{BB}$ is likewise passed into a rectification column $RD_A$ and in $RD_A$ separated into an ROH-comprising vapour stream $S_{B2}$ having a pressure $p_{B2}$ and a temperature $T_{B2}$ at the top of $RD_A$ and a water stream $S_W$ at the bottom of $RD_A$. The vapour stream $S_{BB}$ is passed into a rectification column $RD_A$ in admixture with $S_{AB}$ or separately from $S_{AB}$. The vapour stream $S_{BB}$ is preferably mixed with $S_{AB}$ and then passed into a rectification column $RD_A$.

In one embodiment of the present invention the vapour streams $S_{AB}$ and optionally $S_{BB}$ may be compressed before they are passed to the rectification column $RD_A$. This may be achieved via an optional compressor $VD_{AB1}$.

It will be appreciated that in the embodiments in which $S_{BB}$ is passed into a rectification column $RD_A$ separately from $S_{AB}$, $S_{AB}$ and $S_{BB}$ undergo mixing in the rectification column $RD_A$ so that in any case performance of step (b) results in separation into an ROH-comprising vapour stream $S_{B2}$ at the top of $RD_A$ and a water stream $S_W$ at the bottom of $RD_A$.

The pressure of the vapour stream $S_{B2}$ is referred to as "$p_{B2}$" and its temperature as "$T_{B2}$". This relates in particular to the pressure and temperature of $S_{B2}$ before $S_{B2}$ has been subjected to step (c) of the process according to the invention.

It is preferable when the water stream $S_W$ is also withdrawn at the bottom of the rectification column $RD_A$ in step (b).

Any desired rectification column known to those skilled in the art may be employed as rectification column $RD_A$ in step (b) of the process according to the invention. The reaction column $RD_A$ preferably contains internals. Suitable internals are, for example, trays, unstructured packings or structured packings. Typically employed trays are bubble cap trays, sieve trays, valve trays, tunnel cap trays or slit trays. Unstructured packings are generally random packings. Typically employed packings are Raschig rings, Pall rings, Berl saddles or Intalox® saddles. Structured packings are for example marketed under the trade name Mellapack® from Sulzer. Further suitable internals other than the recited internals are known to those skilled in the art and may likewise be used.

Preferred internals have a low specific pressure drop per theoretical separation stage. By way of example structured packings and random packings have a markedly lower pressure drop per theoretical separation stage than trays. This has the advantage that the pressure drop in the rectification column remains as low as possible and thus the mechanical power of the compressor and the temperature of the alcohol/water mixture to be evaporated remains low.

When the rectification column $RD_A$ contains structured packings or unstructured packings these may be divided or in the form of an uninterrupted packing. However, typically at least two packings are provided, one packing above the feed point of the vapour stream $S_{AB}$/the feed points of the two vapour streams $S_{AB}$ and $S_{BB}$ and a packing below the point of the vapour stream $S_{AB}$/the feed points of the two vapour streams $S_{AB}$ and $S_{B3}$. If an unstructured packing is used, for example a random packing, the packings typically rest on a suitable sieve tray or mesh tray.

In the integrated system comprising reaction column $RR_A$ (or in the embodiment in which step (a2) is performed reaction column $RR_A$ and reaction column $RR_B$) and rectification column $RD_A$ in the process according to the invention the rectification column $RD_A$ is preferably operated at a pressure selected such that the pressure gradient between the columns can be established with little cost and complexity in the case of vapour compression according to step (c).

The alcohol ROH is consumed in the process according to the invention and especially in a continuous process mode therefore requires replacement with fresh alcohol ROH.

Supply of the fresh alcohol ROH is thus especially carried out directly as reactant stream $S_{AE1}$ comprising ROH into the reaction column $RR_A$ or in the embodiments in which step (a2) is performed into the reaction columns $RR_A$ and $RR_B$.

In the process according to the invention it is further preferable to employ the ROH-comprising vapour stream $S_{B2}$ partially as reactant stream $S_{AE1}$ in step (a1) and optionally as reactant stream $S_{BE1}$ in step (a2). The compressed vapour stream $S_{B3}$ may alternatively or in addition be employed partially as reactant stream $S_{AE1}$ in step (a1) and optionally as reactant stream $S_{BE1}$ in step (a2). In this preferred embodiment it is yet more preferable when the fresh alcohol ROH is added to the rectification column $RD_A$.

When the fresh alcohol ROH is added to the rectification column $RD_A$ it is preferably supplied either in the rectifying section of the rectification column $RD_A$ or directly at the top of the rectification column $RD_A$. The optimal feed point depends on the water content or the employed fresh alcohol and also on the desired residual water content in the vapour stream $S_{B2}$. The higher the a portion of water in the employed alcohol and the higher the purity requirements or the vapour stream $S_{B2}$ the more advantageous is a feed a number of theoretical trays below the top of the rectification column $RD_A$. Up to 20 theoretical trays below the top of the rectification column $RD_A$, in particular 1 to 5 theoretical trays, are preferred.

When the fresh alcohol ROH is added to the rectification column $RD_A$ it is added at the top of the rectification column $RD_A$ at temperatures up to boiling point, preferably at room temperature. A dedicated feed may be provided for the fresh alcohol or else when a portion of the alcohol withdrawn at the top of the rectification column $RD_A$ is recycled may be mixed therewith after condensation and supplied to the rectification column $RD_A$ together. In this case it is particularly preferable when the fresh alcohol is added to a condensate container in which the alcohol condensed from the vapour stream $S_{B2}$ is collected.

In an advantageous embodiment of the invention the reaction column $RR_A$ of step (a1), or reaction columns $RR_A$ and $RR_B$ in the above-described preferred embodiment in which step (a2) is performed, and the rectification column $RD_A$ of step (b) for separation of the vapour stream $S_{B1}$ are accommodated in one column shell, wherein the column is at least partially subdivided by at least one dividing wall, or in the above-described preferred embodiment in which step (a2) is performed, by at least two dividing walls, wherein the at least one dividing wall or the at least two dividing walls extend to the bottom of the column. As described at point 4.2 this is then a dividing wall column again.

In this case the reaction to afford the crude product $RP_A$ according to step (a1) or the crude products $RP_A$ and $RP_S$ according to steps (a1) and (a2) are performed in one part of the TRD, wherein the reactant stream $S_{AE2}$ and optionally the reactant stream $S_{BE2}$ are added below but a similar height to the upper end of the dividing wall and the reactant stream $S_{AE1}$ and optionally the reactant stream $S_{BE1}$ are added in vaporous form at the lower end. The alcohol/water mixture formed above the feed point of the reactant stream is then distributed above the dividing wall over the entire column region serving as the rectification portion of the rectification column $RD_A$. The second lower portion of the column separated by the dividing wall is the stripping portion of the rectification column $RD_A$. The energy required for the distillation is then supplied via an evaporator at the lower end of the second portion of the column separated by the dividing wall, wherein this evaporator may be conventionally heated or heated with the compressed vapour stream $S_{B3}$. When the evaporator is conventionally heated an intermediate evaporator heated with a compressed vapour stream $S_{B3}$ may additionally be provided.

The vapour stream $S_{B2}$ comprising ROH is then withdrawn at the top of the rectification column $RD_A$ after step (b) of the process according to the invention. The preferred mass fraction of ROH in this vapour stream $S_{B2}$ is ≥99% by weight, preferably ≥99.6% by weight, more preferably ≥99.9% by weight, wherein the remainder is especially water.

A water stream $S_W$ which may contain <1% by weight of alcohol is obtained at the bottom of $RD_A$.

In the context of the present invention the withdrawal of the ROH-comprising vapour stream $S_{B2}$ at the top of the rectification column $RD_A$ is to be understood as meaning that the vapour stream $S_{B2}$ is withdrawn above the internals in the rectification column $RD_A$ as a top stream or as a sidestream. The preferred withdrawal of the stream $S_W$ containing substantially water at the bottom of the rectification column $RD_A$ is typically carried out at the lower bottom of the rectification column $RD_A$ but the withdrawal may also be carried out via a sidestream takeoff in the bottom.

4.4 Step (c) of the Process According to the Invention

In step (c) of the process according to the invention at least a portion of the vapour stream $S_{B2}$ is compressed. This affords a vapour stream $S_{B3}$ which is compressed with respect to $S_{B2}$. The pressure of the vapour stream $S_{B3}$ is referred to as "$p_{B3}$" and its temperature as "$T_{B3}$".

The pressure $p_{B3}$ of $S_{B3}$ is higher, preferably 1 to 10 bar higher, more preferably 3 to 6 bar higher, yet more preferably 5 bar higher, than the pressure $p_{B2}$ of $S_{B2}$ and the temperature $T_{B3}$ of $S_{B3}$ is higher, preferably 10° C. to 150° C., preferably 50° C. to 100° C. yet more preferably 95° C., than the temperature $T_{B2}$ or $S_{B2}$.

The compressing of the vapour stream $S_{B2}$ in step (c) may be carried out in any desired manner known to those skilled in the art. The compression can therefore be performed for example as a single-stage or multi-stage compression, preferably a multi-stage compression. A multi-stage compression may employ a plurality of compressors of the same type or compressors of different types. The use of single-stage compression or multi-stage compression depends on the pressure to which the vapour SM is to be compressed.

In a preferred embodiment of the process according to the invention 10% to 90% by weight, preferably 20% to 80% by weight, more preferably 30% to 70% by weight, yet more preferably 40% to 60% by weight, yet still more preferably 50% by weight, of the vapour stream $S_{B2}$ is employed as reactant stream $S_{AE1}$ or, when step (a2) is performed, as reactant stream $S_{AE1}$ and/or reactant stream $S_{BE1}$.

It is advantageous when at least the portion employed as reactant stream $S_{AE1}$ and/or reactant stream $S_{BE1}$ is compressed (precompressed) with a first precompressor $VD_{AB2}$. In this preferred embodiment the compressor $VD_{AB1}$ as described hereinabove may also be employed alternatively or in addition to ensure this precompression.

In this preferred embodiment the remaining portion of the vapour stream $S_{B2}$, i.e. the portion not used as reactant stream $S_{AE1}$ and/or reactant stream $S_{BE1}$, is then further compressed and employed in step (d) according to the invention. This additional compression is performed in particular with at least one compressor $VD_1$ additional to $VD_{AB1}$ and $VD_{AB2}$.

The temperature $T_{B3}$ and the pressure $p_{B3}$ to which $S_{B3}$ is compressed in step (c) is adjusted depending on which of $RP_A$, $S_{AE1}$, $S_{AE2}$, $S_{AP}$, $S_{AB}$ in step (a1) or, when step (a2) is performed, which of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ the energy is to be transferred to. It will be appreciated that when one of these components for example is to be heated with $S_{B3}$ the temperature $T_{B3}$ of $S_{B3}$ at the end of step (c) must then be higher than the temperature of the component to be heated in step (d). This can be adjusted by a person skilled in the art according to his knowledge of the art.

The same applies to the pressure $p_3$ to which $S_{B3}$ is to be adjusted. This too can be adjusted by a person skilled in the art according to the requirements in step (d).

When energy from the compressed vapour stream $S_{B3}$ is to be transferred to the crude product $RP_A$ for example and in particular the crude product $RP_A$ is to be heated via an intermediate evaporator $V_{ZA}$ attached to the reaction column $RR_A$ heating of the intermediate evaporator $V_{ZA}$ requires a smaller pressure difference to be overcome than when energy from the vapour stream $S_{B3}$ is employed in step (d) of the process according to the invention for heating an evaporator $V_{SA}$ at the bottom of the reaction column $RR_A$ with which $S_{AP}$ is then heated.

The larger pressure difference to be overcome may be overcome using additional compressor stages or using a stronger compressor. However, additional compressor stages are typically employed.

Any desired compressor known to those skilled in the art and capable of compressing gas streams is suitable as a compressor in the process according to the invention, in particular for compressing the vapour stream $S_{B2}$. Suitable compressors are for example single-stage or multi-stage turbines, piston compressors, screw compressors, centrifugal compressors or axial compressors.

In a multi-stage compression, compressors suitable for the respective pressure stages to be overcome are employed.

4.5 Step (d) of the Process According to the Invention

In step (d) of the process according to the invention energy is transferred from step $S_{B3}$ to at least one of $RP_A$, $S_{AE1}$, $S_{AE2}$, $S_{AP}$, $S_{AB}$, preferably at least one of $RP_A$. $S_{AP}$, yet more preferably $S_{AP}$. In the optional embodiment of the process according to the invention in which step (a2) is performed energy is alternatively or in addition, preferably in addition, transferred from $S_{B3}$ to at least one of $RP_B$, $S_{BE1}$, $S_{BE2}$, $S_{BP}$, $S_{BB}$, preferably at least one of $RP_B$, $S_{BP}$, more preferably $S_{BP}$.

When step (a2) is performed step (d) of the process according to the invention accordingly comprises transferring energy from $S_{B3}$ to at least one of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$, preferably at least one of $RP_A$, $S_{AP}$, $RP_B$, SP, preferably to both $S_{AP}$ and $S_{BP}$.

This affords a vapour $S_{B4}$ having a lower energy content than $S_{B3}$. This is to be understood as meaning in particular that for the pressure $p_{B4}$ of $S_{B4}$ and the temperature $T_{B4}$ of $S_{B4}$:$p_{B4} \leq p_{B3}$ and $T_{B4} < T_{B3}$. It is yet more preferable when $T_{B2} < T_{B4}$ and $p_{B2} < p_{B4}$, so that $T_{B2} < T_{B4} < T_{B3}$ and $p_{B2} < p_{B4} \leq p_{B3}$.

This is to be understood as meaning in particular that $S_{B3}$ is used to heat at least one of $RP_A$, $S_{AE1}$, $S_{AE2}$, $S_{AP}$, $S_{AB}$, preferably at least one of $RP_A$, $S_{AP}$, yet more preferably $S_{AP}$.

In the optional embodiment of the process according to the invention in which step (a2) is performed this is to be understood as meaning in particular that alternatively or in addition, preferably in addition. $S_{B3}$ is used to heat at least one of $RP_B$, $S_{BE1}$, $S_{BE2}$, $S_{BP}$, $S_{BB}$, preferably at least one of $RP_B$, $S_{BP}$, preferably $S_{BP}$.

When step (a2) is performed it is yet more preferable to use $S_{B3}$ to heat at least one of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$, preferably at least one of $RP_A$, $S_{AP}$, $RP_B$, $S_{BP}$, preferably both $S_{AP}$ and $S_{BP}$.

Accordingly after performing step (c) of the process according to the invention the temperature $T_{B3}$ of $S_{B3}$ is preferably higher than that of a component selected from $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ which is heated by $S_{B3}$ in step (d).

The transfer of energy to, preferably the heating of, at least one of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ by $S_{B3}$ is preferably carried out directly or indirectly.

"Directly" is to be understood as meaning that $S_{B3}$ is contacted with the at least one component selected from $RP_A$, $S_{AE1}$, $S_{AE2}$, $S_{AP}$, $S_{AB}$ or, when step (a2) is performed, selected from $RP_A$, $S_{AE1}$, $S_{AE2}$, $S_{AP}$, $S_{AB}$, $RP_B$, $S_{BE1}$, $S_{BE2}$, $S_{SB}$, $S_{BB}$ so that heat from $S_{B3}$ is transferred to the relevant at least one component.

In the case of $S_{AP}$, $S_{BP}$ this may be performed when $S_{B3}$ is at least partially passed through a bottoms evaporator $V_{SA}/V_{SB}$ on the reaction column $RR_A/RR_B$ and heats $S_{AP}/S_{BP}$ therein.

Employable heat exchangers include the heat exchangers familiar to those skilled in the art.

"Indirect" is to be understood as meaning in particular that $S_{B3}$ is contacted with at least one heat transfer medium $W_1$, preferably via at least one heat exchanger $WT_X$, wherein the heat transfer medium is not $RP_A$, $S_{AE1}$, $S_{AE2}$, $S_{AP}$, $S_{AB}$, $RP_B$, $S_{BE1}$, $S_{BE2}$, $S_{BP}$ or $S_{BB}$, i.e. is distinct therefrom, so that energy, preferably heat, is transferred from $S_{B3}$ to the at least one heat transfer medium $W_1$ and the heat is then transferred from $W_1$ to the relevant at least one component selected from $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ when $W_1$ contacts the relevant component.

In a further embodiment of the process according to the invention indirect heating of at least one of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ with $S_{B3}$ may comprise transferring heat initially from $S_{B3}$ to $W_1$, preferably by contacting via at least one heat exchanger $WT_X$ and subsequently transferring from $W_1$ to a further heat transfer medium $W_2$ distinct from $RP_A$, $S_{AE1}$, $S_{AE2}$, $S_{AP}$, $S_{AB}$, $RP_B$, $S_{BE1}$, $S_{BE2}$, $S_{BP}$, $S_{BB}$ preferably by contacting via at least one heat exchanger $WT_Y$. The last step comprises transferring the heat from $W_2$ to at least one of $RP_A$, $S_{AE1}$, $S_{AE2}$, $S_{AP}$, $S_{AB}$, $RP_B$, $S_{BE1}$, $S_{BE2}$, $S_{BP}$, $S_{BB}$. It will be appreciated that still further heat transfer media $W_3$, $W_4$, $W_5$ etc. may accordingly be employed in further embodiments of the present invention.

Utilizable heat transfer medium $W_1$ and further heat transfer media $W_2$, $W_3$, $W_4$, $W_5$ include any heat transfer media known to those skilled in the art, preferably selected from the group consisting of water; alcohol-water solutions; salt-water solutions, also including ionic liquids such as for example LiBr solutions, dialkyhmidazolium salts such as especially dialkylimidazolium dialkylphosphates; mineral oils, for example diesel oils, thermal oils such as for example silicone oils; biological oils such as for example limonenes; aromatic hydrocarbons such as for example dibenzyltoluene. The most preferred transfer medium $W_1$ is water.

Salt-water solutions that may be used are also described for example in DE 10 2005 028 451 A1 and WD 2006/134015 A1.

The transfer of energy from $S_{B3}$ to the crude product $RP_A$, $RP_B$ and/or at least one stream selected from $S_{AE1}$, $S_{AE2}$, $S_{AP}$, $S_{AB}$, $S_{BE1}$, $S_{BE2}$, $S_{BP}$, $S_{BB}$ is carried out by the processes known to those skilled in the art and preferably by any of the embodiments recited hereinbelow under 4.5.1, 4.5.2, 4.5.3 and 4.5.4, wherein the embodiment recited under 4.5.4 is most preferred.

4.5.1) In the embodiment of the present invention in which in step (d) energy is transferred from $S_{B3}$ to at least one of $RP_A$ and/or $RP_B$ this is preferably carried out such that the reaction column $RR_A/RR_B$ has attached to it at least one intermediate evaporator $V_{ZA}/V_{ZB}$ by means of which a liquid crude product $RP_A/RP_B$ is evaporated inside the reaction column $RR_A/RR_B$. In this preferred embodiment this intermediate evaporator $V_{ZA}/V_{ZB}$ in particular is heated with $S_{B3}$ in the case of direct heating or heated with a heat transfer medium $W_1$ distinct from $S_{B3}$ in the case of indirect heating, wherein the heat transfer medium $W_1$ has previously absorbed energy from $S_{B3}$.

4.5.2) In the embodiment of the present invention in which in step (d) energy is transferred from $S_{B3}$ to the at least one reactant stream selected from $S_{AE1}$, $S_{AE2}$, $S_{BE1}$, $S_{BE2}$ this is preferably carried out such that the respective reactant stream passes through at least one heat exchanger WT1 before it is passed into the reaction column $RR_A/RR_B$. WT1 effects transfer of energy, preferably heat, from $S_{B3}$ in the case of direct heating or from a heat transfer medium $W_1$ distinct from $S_{B3}$ in the case of indirect heating, wherein the heat transfer medium $W_1$ has previously absorbed energy from $S_{B3}$, to at least one reactant stream $S_{AE1}$, $S_{AE2}$, $S_{BE1}$, $S_{BE2}$.

4.5.3) In the embodiment of the present invention in which in step (d) energy is transferred from $S_{B3}$ to at least one vapour stream selected from $S_{AB}$, $S_{BB}$ this is preferably carried out such that the respective vapour stream passes through a heat exchanger WT2 before it is passed into the rectification column $RD_A$. WT2 effects transfer of energy, preferably heat, from $S_{B3}$ in the case of direct heating or from a heat transfer medium $W_1$ distinct from $S_{B3}$ in the case of indirect heating, wherein the heat transfer medium $W_1$ has previously absorbed energy from $S_{B3}$, to the at least one vapour stream selected from $S_{AB}$, $S_{BB}$.

4.5.4) In the embodiment of the present invention in which in step (d) energy is transferred directly from $S_{B3}$ to at least one bottoms product stream selected from $S_{AP}$, $S_{BP}$ this is advantageously effected such that the reaction column $RR_A/RR_B$ has attached to it at least one bottoms evaporator $V_{SA}/N_{SB}$ through which $S_{B3}$ is at least partially passed and through which $S_{AP}/S_{BP}$ are at least partially passed after exiting the reaction column $RR_A/RR_B$ so that energy, preferably heat, is transferred from $S_{B3}$ to $S_{AP}/S_{BP}$, in particular so that $S_{AP}/S_{BP}$ is at least partially evaporated, in particular ROH is at least partially evaporated from $S_{AP}/S_{BP}$, to afford a bottoms product stream $S_{AP}/S_{BP}$'.

In the embodiment of the present invention in which in step (d) energy is indirectly transferred from $S_{B3}$ to at least one bottoms product stream selected from $S_{AP}$, $S_{BP}$ this is advantageously effected such that preferably via a heat exchanger $S_{B3}$ contacts a heat transfer medium $W_1$ distinct from $RP_A$, $S_{AE1}$, $S_{AE2}$, $S_{AP}$, $S_{AB}$, $RP_B$, $S_{BE1}$, $S_{BE2}$, $S_{BP}$ or $S_{BB}$, preferably water, so that energy, preferably heat, is transferred from $S_{B3}$ to the at least one heat transfer medium $W_1$ and the reaction column $RR_A/RR_B$ has attached to it at least one bottoms evaporator $V_{SA}/V_{SB}$ through which $W_1$ is at least partially passed and through which $S_{AP}/S_{BP}$ are at least partially passed after exiting the reaction column $RR_A/RR_B$ so that energy, preferably heat, is transferred from $W_1$ to $S_{AP}/S_{BP}$, in particular so that $S_{AP}/S_{SB}$ is at least partially evaporated, in particular ROH is at least partially evaporated from $S_{AP}/S_{BP}$, to afford a bottoms product stream $S_{AP}/S_{BP}$''.

In the preferred embodiment according to 4.5.4 it is yet more preferable when in addition to the evaporator $V_{SA}/V_{SB}$ at least one further conventionally heated evaporator $V_{KA}$ on the reaction column $RR_A/V_{KB}$ on the reaction column $RR_B$ is employed and arranged at the bottom of the reaction column $RR_A/RR_B$. When the evaporator $V_{SA}/V_{SB}$ directly or indirectly heated with vapour stream $S_{B3}$ is likewise arranged at the bottom of the reaction column $RR_A/RR_B$ the conventionally heated evaporator $V_{KA}/V_{KB}$ may for example be utilized to supply additional heat during operation of the reaction column $RR_A/RR_B$. However, the conventionally heated evaporator $V_{KA}/V_{KB}$ is generally utilized to start up the reaction column $RR_A/RR_B$. During startup of the reaction column $RR_A/RR_B$ there is still insufficient vapour $S_{B3}$ to a flow direct or indirect heating of the evaporator $V_{SA}/V_{SB}$ and heat must therefore initially be supplied from an external source. Startup or the rectification column $RD_A$ is followed by an increase in the amount of vapour $S_{B2}$ withdrawable at the top of the reaction column $RD_A$. This may then be compressed to afford $S_{B3}$ and operation may be transferred to the evaporator $V_{SA}/V_{SB}$ heated with the compressed vapour stream $S_{B3}$. It is thus possible to slowly start up the evaporator $V_{SA}/V_{SB}$ which is heated with the vapour stream $S_{B3}$ and correspondingly reduce the heating of the conventionally heated evaporator $V_{KA}/V_{KB}$ or to wait until a steady operating state has been established in the rectification column $RR_A/RR_B$ and then switch from the conventionally heated evaporator $V_{KA}/V_{KB}$ to the evaporator $V_{SA}/V_{SB}$ heated with the compressed vapour stream $S_{B3}$.

When the compressed vapour stream $S_{B3}$ is used to heat an intermediate evaporator $V_{ZA}/V_{ZB}$ as in the embodiment of the present invention described under point 4.5.1 for example the additional conventionally heated evaporator $V_{KA}/V_{KB}$ is utilized to introduce further heat into the reaction column $RR_A/RR_B$ at the bottom of the reaction column $RR_A/RR_B$. In this case the conventionally heated evaporator $V_{KA}/V_{KB}$ is operated over the entire operating duration of the reaction column $RR_A/RR_B$. Here too, startup of the reaction column $RR_A/RR_B$ requires that a greater amount of heat is initially introduced into the reaction column $RR_A$/$RR_B$ via the conventionally heated evaporator $V_{KA}$/$V_{KB}$ until the intermediate evaporator $V_{ZA}$/$N_{ZB}$ can be provided with a sufficiently large vapour stream $S_{B3}$ to effect heating thereof. The amount of heat introduced into the reaction column $RR_A$/$RR_B$ with the conventionally heated evaporator $V_{KA}$/$V_{KB}$ may then be reduced. When using an intermediate evaporator $V_{ZA}$/$V_{ZB}$ it is alternatively also possible to employ two conventionally heated evaporators $V_{KA1}$ and $V_{KA2}$/$V_{KB1}$ and $V_{KB2}$ at the bottom of the respective reaction column $RR_A$/$RR_B$. The additional conventionally heated evaporator $V_{KA2}$/$W_{KB2}$ is then utilized to start up the column and the other conventionally heated evaporator $V_{KA1}$/$V_{KB1}$ continues to be operated during operation of the reaction column $RR_A$/$RR_B$.

Step (d) of the process according to the invention reflects the unexpected effect of the present invention. The inventive process makes it possible to prevent the excess energy obtained during compression of the vapour stream $S_{B2}$ to afford the compressed vapour stream $S_{B3}$ from dissipating without being utilized but rather to employ it to operate the conversion in the reactive distillation. This results in a marked energy saving.

4.6 Preferred Step (e) of the Process According to the Invention

In a preferred embodiment of the process according to the invention the vapour stream $S_{B4}$ is used for heating the rectification column $RD_A$ in a step (e). This may be achieved in particular when the lower end thereof has attached to it a bottoms evaporator $V_{SRD}$ which heats the water stream $S_W$ at the bottom of $RD_A$. The water stream $S_W$ may thus be at least partially recycled back into the rectification column $RD_A$. Alternatively or in addition, preferably in addition, the vapour stream $S_{B4}$ may also be recycled back into the rectification column $RD_A$, preferably at the top thereof. When the vapour stream $S_{B4}$ is recycled into the rectification column $RD_A$ it is preferably condensed and preferably added at the top of the rectification column $RD_A$ at temperatures up to boiling point, preferably at room temperature. A dedicated feed may be provided for the vapour stream $S_{B4}$ or else when a portion of the alcohol withdrawn at the top of the rectification column $RD_A$ is recycled may be mixed therewith after condensation and supplied to the rectification column $RD_A$ together. In this case it is particularly preferable when the vapour stream $S_{B4}$ is added to a condensate container in which the alcohol condensed from the vapour stream $S_{B2}$ is collected.

When the vapour stream $S_{B4}$ is employed in step (e) it is advantageous to compress said stream and at least one further compressor $VD_x$ to obtain a vapour stream $S_{B5}$ compressed with respect to $S_{B4}$.

PREFERRED EMBODIMENTS OF THE INVENTION

Figure 1:
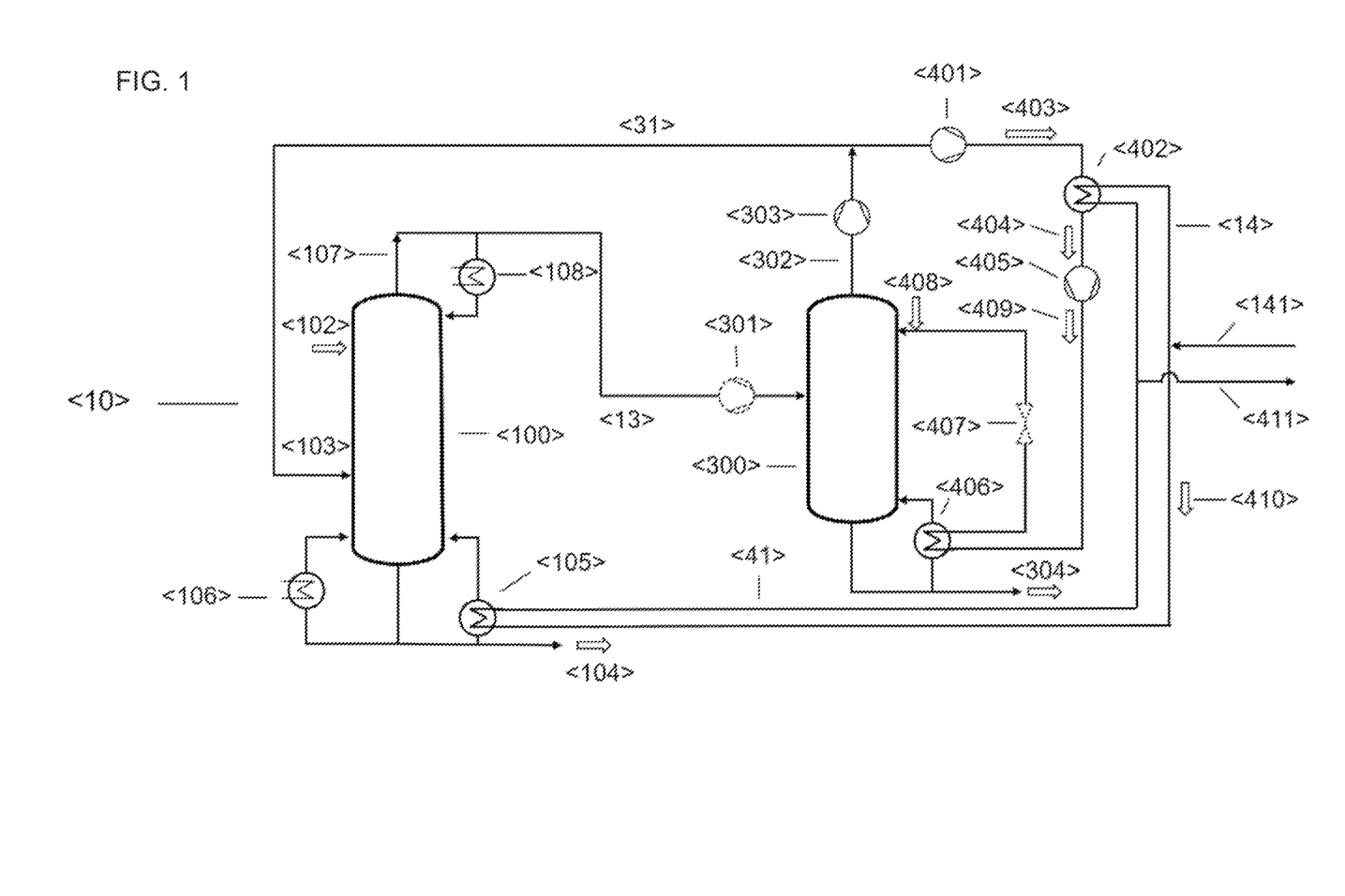
FIG. 1 shows an embodiment of the process according to the invention in which in a reaction column $RR_A$ <100> NaOH $S_{AE2}$ <102> is reacted with methanol $S_{AE1}$ <103> to afford sodium methoxide <104>. A methanol-methoxide mixture $S_{AP}$, <104> is withdrawn at the bottom of the reaction column. The obtained vapour $S_{AB}$ <107> is supplied to a water/methanol column $RD_A$ <300> in which methanol is distillatively recovered as vapour $S_{B2}$ <302>. The vapour $S_{B2}$ <302> is precompressed using compressor $VD_{AB2}$ <303> and in compressor $VD_1$ <401> compressed to afford vapour $S_{B3}$ <403>. The energy removed after the compression of the vapour $S_{B3}$ <403> in the intermediate cooler $WT_X$ <402> is supplied to the evaporator $V_{SA}$ <105> at the bottom of the reaction column $RR_A$ <100>. After removal of the energy the obtained vapour $S_{B4}$ <404> is optionally recompressed using compressor $VD_x$ <405> and the thus obtained vapour $S_{B5}$ <409> supplied to the evaporator $V_{SRD}$ <408> at the bottom of the rectification column $RD_A$ <300> for heating.

FIG. 1 shows an embodiment <10> of the process according to the invention. It comprises a reaction column $RR_A$ <100> which may optionally comprise stages above the reactant stream $S_{AE2}$ <102>. At the top of the reaction column $RR_A$ <100> an aqueous NaOH solution is added as reactant stream $S_{AE2}$ <102>, it is alternatively also possible to add a methanolic KOH solution as reactant stream $S_{AE2}$ <102> in order then to produce the corresponding potassium methoxide. Above the bottom of the reaction column $RR_A$ <100> methanol is added in vaporous form as reactant stream $S_{AE1}$ <103>. The product sodium methoxide dissolved in methanol is obtained at the bottom of the reaction column $RR_A$ <100> as bottoms product stream $S_{AP'}$ <104>. The bottoms evaporator $V_{SA}$ <105> and the optional evaporator $V_{KA}$ <106> at the bottom of the column $RR_A$ <100> are used to adjust the concentration of the sodium methoxide solution $S_{AP'}$ <104> to the desired value. The optional evaporator $V_{KA}$ <106> is especially also used to start up the column $RR_A$ <100>.

At the top of the reaction column $RR_A$ <100> a vapour stream $S_{AB}$ <107> is withdrawn. At the top of the reaction column $RR_A$ <100> a portion of the vapour stream $S_{AB}$ <107> is condensed in the condenser $K_{RRA}$ <108> and applied in liquid form to the top of the reaction column $RR_A$ <100> as reflux. However, condenser $K_{RRA}$ <108> and the adjustment of the reflux are optional.

The vapour stream $S_{AB}$ <107> is supplied via conduit <13> to a rectification column $RD_A$ <300>.

At the top of the rectification column $RD_A$ <300> methanol vapour $S_{B2}$ <302> is discharged. Said vapour is then passed through the compressor $VD_{AB2}$ <303> and partially recycled via conduit <31> to the reaction column $RR_A$ <100> where it is employed as reactant stream $S_{AE1}$ <103>. Compressor $VD_{AB1}$ <301> may also be employed alternatively or in addition to the compressor $VD_{AB2}$ <303>.

The invention provides that after passage through the compressor $VD_{AB2}$ <303> and precompression therein at least a portion of the methanol vapour $S_{B2}$ <302> is passed to compressor $VD_1$ <401> where it is compressed to afford compressed vapour stream $S_{B3}$<403>. The vapour stream $S_{B3}$ <403> heats the bottoms evaporator $V_{SA}$ <105>. This may be effected through direct heating of bottoms evaporator $V_{SA}$ <105> by $S_{B3}$ <403> (not shown in FIG. 1). Heating is alternatively effected as shown in FIG. 1 by using heat exchanger $WT_X$ <402> to transfer heat to a heat transfer medium (preferably water) $W_1$ <410> by means of which the bottoms evaporator $V_{SA}$ <105> is in turn heated. The heat transfer medium (preferably water) $W_1$ <410> is circulated in the conduits <41> and <14> which may optionally also comprise conduits <141> and <411> for control purposes. After passage through the heat exchanger $WT_X$ <402> a vapour stream $S_{B4}$ <404> having a reduced energy content compared to $S_{B3}$ <403> is obtained. $S_{B4}$ <404> passes through an additional compressor $VD_x$ <405> and is then utilized as vapour stream $S_{B5}$ <409> compressed with respect to $S_{B4}$ <404> for heating bottoms evaporator $V_{SRO}$ <406> after which it is passed through an optional throttle <407> and optionally with fresh methanol <408> sent back to the rectification column $RD_A$ <300> as reflux. At the bottom of the rectification column $RD_A$ <300> a water stream $S_W$ <304> is obtained.

Figure 2:
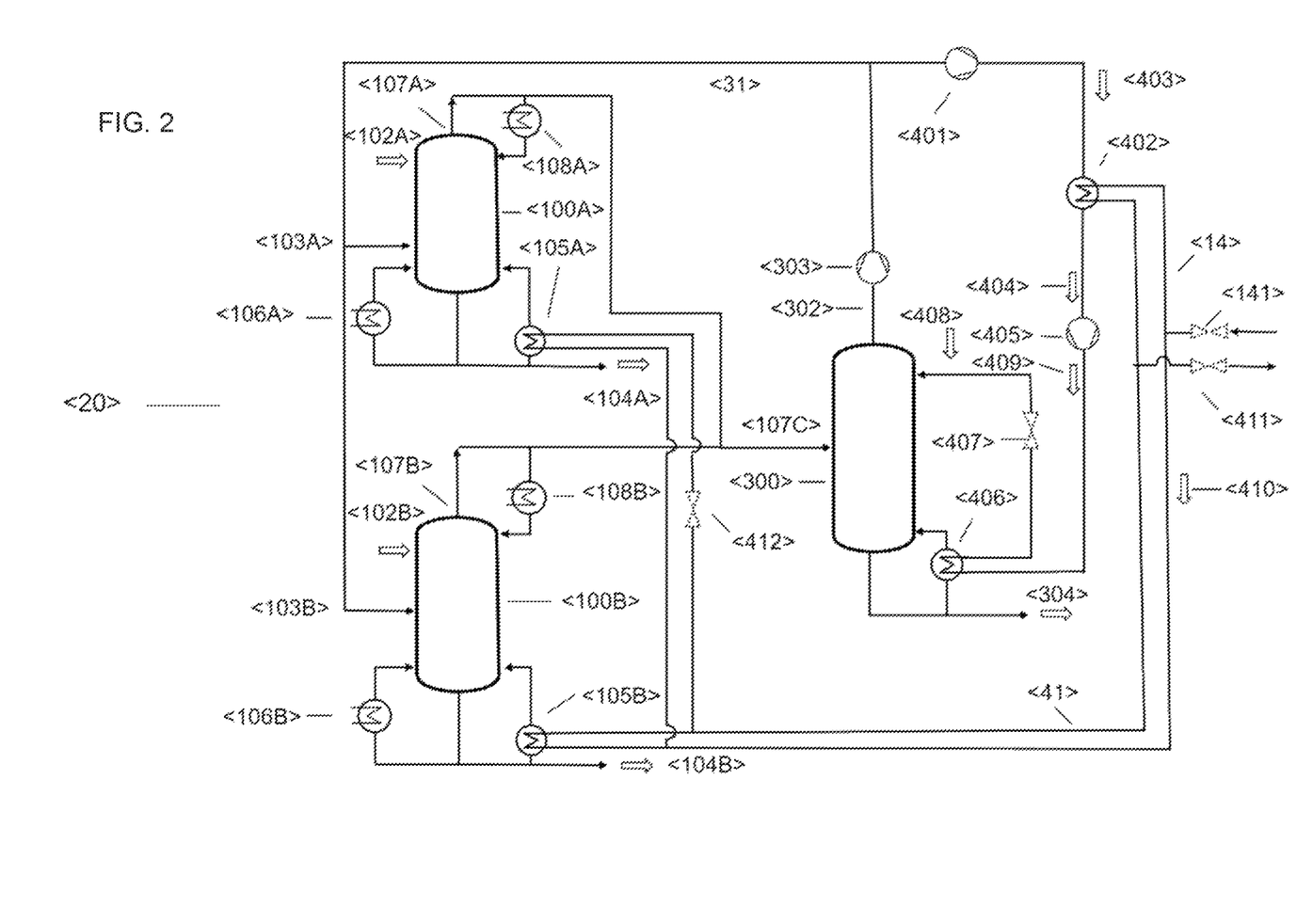
FIG. 2 shows an embodiment of the process according to the invention in which in each case in two separate reaction columns $RR_A$ <100A>, $RR_B$ <100B> NaOH $S_{AE2}$ <102A> and KOH $S_{BE2}$ <102B> are reacted with methanol $S_{AE2}$<103A>/$S_{BE2}$<103B> to afford the respective methoxide. The methanol-methoxide mixture $S_{AP}$, <104A> and $S_{BP}$, <104B> is in each case withdrawn at the bottom of the reaction columns. The obtained vapours are supplied as mixture <107C> to a water/methanol column $RD_A$<300> in which methanol is distillatively recovered as vapour $S_{B2}$ <302>. Said vapour $S_{B2}$ <302> is precompressed using compressor $VD_{AB2}$ <303> and using compressor $VD_1$ <401> compressed to afford compressed vapour $S_{B3}$ <403>. The energy removed from the compressed vapour $S_{B3}$ <403> in the intermediate cooler $WT_X$ <402> is supplied to the evaporator $V_{SA}$ <105A> at the bottom of the reaction column $RR_A$ <100A> and the evaporator $V_{SB}$ <105B> at the bottom of the reaction column $RR_B$ <100B>. After the intermediate cooler $WT_X$ <402> the obtained vapour $S_{B4}$ <404> optionally passes through a further compressor $VD_x$ <405> and is supplied as vapour $S_{B4}$ <409> for heating the evaporator $V_{SRD}$ <406> at the bottom of the rectification column $RD_A$ <300>.

FIG. 2 shows a further preferred embodiment of the present invention This corresponds to FIG. 1 with the exception that two reaction columns $RR_A$ <100A> and $RR_B$ <100B> are present and the corresponding constituents of the reaction columns $RR_A$ <100A> and $RR_B$<100B> correspond to those specified in FIG. 1 for the reaction column $RR_A$ <100> wherein each constituent has the further suffix "A"/"B" to signify affiliation to $RR_A$/$RR_B$. In reaction column $RR_A$ <100A> a stream $S_{AE2}$ <102A> comprising NaOH is added and in reaction column $RR_B$ <100B> a stream $S_{BE2}$ <102B> comprising KOH is added. Both reaction columns $RR_A$ <100A> and $RR_B$ <100B> may comprise additional stages above the feed of the alkali metal hydroxide solution but this is optional and not shown in FIG. 2. In contrast to FIG. 1 the conduits <14> and <41> have branchings which allow heat exchange between the vapour $S_{B3}$ <403> with both evaporators $V_{SA}$ <105A> and $V_{SB}$ <105B>. An additional throttle <412> for control purposes may also be included. Vapour stream $S_{AB}$ <107A> and vapour stream $S_{BB}$ <107B> are supplied to the rectification column $RD_A$ <300> in mixed form as vapour stream <107C>.

EXAMPLES

Example 1 (Non-Inventive)

A stream of aqueous NaOH (50% by weight) of 2 kg/h is supplied to the top of a reaction column at 30° C. A vaporous methanol stream of 21 kg/h is supplied in countercurrent above the bottom of the reaction column. The reaction column is operated at a pressure of 1.2 mbar. At the bottom of the column a virtually water-free product stream of 4.5 kg/h is withdrawn (30% by weight sodium methoxide in methanol). At the evaporator of the reaction column about 0.5 kW of heating power is introduced using low pressure steam. A vaporous methanol-water stream of 18.5 kg/h is withdrawn at the top or the reaction column and supplied to a rectification column. The rectification column is operated at about 1.1 bar. At the bottom of the rectification column a liquid water stream of 1.5 kg/h is discharged. At the top of the rectification column a vaporous methanol stream of 33.4 kg/h is withdrawn, preheated to 75° C. In a heat exchanger and then supplied to a first compressor. In this compressor the stream is compressed to 1.7 bar. The stream is subsequently divided and a stream or 21 kg/h is recycled to the reaction column. The remainder of 12.4 kg/h is supplied to a two-stage compression with intermediate cooling. Compressor 2 compresses the stream to 4.9 bar and 180° C. In the subsequent intermediate cooling the stream is cooled to about 150° C. and about 0.2 kW of heat is removed via cooling water. Compressor 3 finally compresses the stream to 6.2 bar and 170° C. In the subsequent condenser which is simultaneously the evaporator for the rectification column about 4 kW of heating power is provided for the rectification column. 3.9 kg/h of fresh methanol is supplied to the liquid methanol stream and the mixed stream is applied to the top of the rectification column as reflux.

Example 2 (Inventive), Corresponds to FIG. 1

Identical to example 1 with the exception that the reaction column <100> comprises two bottoms evaporators <105> and <106>. In the first bottoms evaporator <105> a heat transfer medium is used to introduce a heat flow of about 0.2 kW which is removed and transferred to the heat transfer medium (water) in the intermediate cooling between compressor 2 and 3. The second bottoms evaporator provides the remainder of the required energy via low pressure steam. This reduces the demand for low pressure steam for the reaction column <100> by about 40% compared to the example 1.

Example 3 (Inventive), Corresponds to FIG. 2

A first reaction column is operated identically to example 2. In addition a second reaction column ("K2") is operated with aqueous KOH (50% by weight). As in example 2 both reaction columns each have two bottoms evaporators. A stream of 0.5 kg/h is supplied to the top or K2 at 30° C. A vaporous methanol stream of 7.5 kg/h is supplied in countercurrent above the bottom of K2. K2 is operated at a pressure of 1.2 bar. At the bottom of K2 a virtually water-free product stream of 1.5 kg/h is withdrawn (32% by weight potassium methoxide in methano). In both evaporators of K2 altogether about 0.2 kW of heating power is introduced.

A vaporous methanol-water stream of 7 kg/h is withdrawn at the top of K2. This methanol-water stream is combined with the methanol-water stream from the first reaction column and supplied to the rectification column. The rectification column is operated at about 1.1 bar. At the bottom of the rectification column a liquid water stream of 1.8 kg/h is discharged. At the top of the rectification column a vaporous methanol stream of 46.2 kg/h is withdrawn, preheated to 75° C. in a heat exchanger and then supplied to a first compressor. In this compressor the stream is compressed to 1.7 bar. The stream is subsequently divided and a stream or 28.5 kg/h is recycled to the reaction columns. The remainder of 17.7 kg/h is supplied to a two-stage compression with intermediate cooling. Compressor 2 compresses the stream to 4.9 bar and 180° C. In the subsequent intermediate cooling the stream is cooled to about 140° C. and about 0.36 kW of heat is removed via water as heat transfer medium. Compressor 3 finally compresses the stream to 6.2 bar and 160° C. In the subsequent condenser which is simultaneously the evaporator for the rectification column <300> about 5 kW of heating power is provided for the rectification column. 4.7 kg/h of fresh methanol is supplied to the liquid methanol stream and the mixed stream is applied to the top of the rectification column as reflux. The heat transfer medium heated in the compressor intermediate cooling is utilized to introduce energy via the evaporators of the two reaction columns. In this way about 51% of the required heating power can be provided via the intermediate cooling. Only the remaining 49% must be provided via the evaporators using low pressure steam.

Result: The present invention allows for efficient use of the energy which would otherwise dissipate without being utilized in the intermediate cooling of the compressor stages.

The invention claimed is:

1. A process for producing at least one alkali metal alkoxide of formula $M_AOR$, wherein R is a $C_1$ to $C_6$ hydrocarbon radical and wherein $M_A$ is a metal selected from the group consisting of sodium and potassium, the process comprising:
 (a1) reacting a reactant stream $S_{AE1}$ comprising ROH with a reactant stream $S_{AE2}$ comprising $M_AOH$, in countercurrent in a reaction column $RR_A$, to afford a crude product $RP_A$ comprising $M_AOR$, water, the ROH, and the $M_AOH$,
  wherein a bottoms product stream $S_{AP}$ comprising the ROH and the $M_AOR$ is withdrawn at a lower end of the reaction column $RR_A$, and a vapour stream $S_{AB}$ comprising the water and the ROH is withdrawn at an upper end of the reaction column $RR_A$, and
 (a2) optionally, simultaneously with and spatially separate from (a1), reacting a reactant stream $S_{BE1}$ comprising ROH with a reactant stream $S_{BE2}$ comprising $M_BOH$, in countercurrent in a reaction column $RR_B$, to afford a crude product $RP_B$ comprising $M_BOR$, water, the ROH, and the $M_BOH$,
  wherein $M_B$ is a metal selected from the group consisting of sodium and potassium, and
  wherein a bottoms product stream $S_{BP}$ comprising the ROH and the $M_BOR$ is withdrawn at a lower end of the reaction column $RR_B$ and a vapour stream $S_{BB}$ comprising the water and the ROH is withdrawn at an upper end of the reaction column $RR_B$,
 (b) passing the vapour stream $S_{AB}$ and, if (a2) is performed, the vapour stream $S_{BB}$, in admixture with the vapour stream $S_{AB}$ or separately from the vapour stream $S_{AB}$, into a rectification column $RD_A$, and separating $S_{AB}$ and optionally $S_{BB}$ in the rectification column $RD_A$ into an ROH-comprising vapour stream $S_{B2}$ having a pressure $p_{B2}$ and a temperature $T_{B2}$ at a top of the rectification column $RD_A$ and a water stream $S_W$ at a bottom of the rectification column $RD_A$, (c) compressing at least a portion of the vapour stream $S_{B2}$ to obtain a vapour stream $S_{B3}$ compressed with respect to the vapour stream $S_{B2}$, and having a pressure $p_{B3} > p_{B2}$ and a temperature $T_{B3} > T_{B2}$, and (d) transferring energy from the vapour stream $S_{B3}$ to at least one selected from the group consisting of the crude product $RP_A$, the reactant stream $S_{AE1}$, the reactant stream $S_{AE2}$, the bottoms product stream $S_{AP}$, and the vapour stream $S_{AB}$ and, if (a2) is performed, alternatively or additionally, transferring energy from the vapour stream $S_{B3}$ to at least one selected from the group consisting of the crude product $RP_B$, the reactant stream $S_{BE1}$, the reactant stream $S_{BE2}$, the bottoms product stream $S_{BP}$, and the vapour stream $S_{BB}$, to obtain a vapour stream $S_{B4}$ having a lower energy content than the vapour stream $S_{B3}$.

2. The process according to claim 1, wherein R is methyl or ethyl.

3. The process according to claim 1, wherein the reactant stream $S_{AE2}$ further comprises at least one further compound selected from the group consisting of water and ROH, and
wherein if (a2) is performed, the reactant stream $S_{BE2}$ further comprises at least one further compound selected from the group consisting of and ROH.

4. The process according to claim 1, wherein the rectification column $RD_A$, the reaction column $RR_A$ and, if (a2) is performed, the reaction column $RR_B$ are accommodated in one column shell in a combined column,
wherein the combined column is at least partially subdivided by at least one dividing wall and, if (a2) is performed, by at least two dividing walls,
wherein the at least one dividing wall or the at least two dividing walls extend to a bottom of the combined column.

5. The process according to claim 1, wherein 10% to 90% by weight of the vapour stream $S_{B2}$ is employed as the reactant stream $S_{AE1}$ and, if (a2) is performed, the vapour stream $S_{B2}$ is employed alternatively or additionally as the reactant stream $S_{BE1}$.

6. The process according to claim 1, wherein in step (d), the vapour stream $S_{B3}$ is used to heat at least one selected from the group consisting of the crude product $RP_A$, the reactant stream $S_{AE1}$, the reactant stream $S_{AE2}$, the bottoms product stream $S_{AP}$, and the vapour stream $S_{AB}$, and
wherein if (a2) is performed, alternatively or additionally, the vapour stream $S_{B3}$ is used to heat at least one selected from the group consisting of the crude product $RP_B$, the reactant stream $S_{BE1}$, the reactant stream $S_{BE2}$, the bottoms product stream $S_{BP}$, and the vapour stream $S_{BB}$.

7. The process according to claim 1, wherein the reaction column $RR_A$ comprises at least one evaporator, and
wherein, if (a2) is performed, the reaction column $RR_B$ comprises at least one evaporator.

8. The process according to claim 7, wherein the reaction column $RR_A$ comprises at least one bottoms evaporator $V_{SA}$, and
wherein, if (a2) is performed, the reaction column $RR_B$ comprises at least one bottoms evaporator $V_{SB}$.

9. The process according to claim 8, wherein the vapour stream $S_{B3}$ is at least partially passed through the at least one bottoms evaporator $V_{SA}$ on the reaction column $RR_A$, and the bottoms product stream $S_{AP}$ is at least partially passed through the at least one bottoms evaporator $V_{SA}$ so that energy is transferred from the vapour stream $S_{B3}$ to the bottoms product stream $S_{AP}$, and
wherein if (a2) is performed, alternatively or in addition, the vapour stream $S_{B3}$ is at least partially passed through the at least one bottoms evaporator $V_{SB}$ on the reaction column $RR_B$ and the bottoms product stream $S_{BP}$ is at least partially passed through the at least one bottoms evaporator $V_{SB}$, so that energy is transferred from the vapour stream $S_{B3}$ to the bottoms product stream $S_{BP}$.

10. The process according to claim 8, wherein the vapour stream $S_{B3}$ contacts at least one heat transfer medium $W_1$ distinct from the crude product $RP_A$, the reactant stream $S_{AE1}$, the reactant stream $S_{AE2}$, the bottoms product stream $S_{AP}$, the vapour stream $S_{AB}$, the crude product $RP_B$, the reactant stream $S_{BE1}$, the reactant stream $S_{BE2}$, the bottoms product stream $S_{BP}$, and the vapour stream $S_{BB}$, so that energy is transferred from the vapour stream $S_{B3}$ to the at least one heat transfer medium $W_1$, and
wherein the at least one heat transfer medium $W_1$ is then at least partially passed through the at least one bottoms evaporator $V_{SA}$ on the reaction column $RR_A$ and the bottoms product stream $S_{AP}$ is at least partially passed through the at least one bottoms evaporator $V_{SA}$, to transfer energy from the at least one heat transfer medium $W_1$ to the bottoms product stream $S_{AP}$, and
wherein if (a2) is performed, alternatively or in addition, the at least one heat transfer medium $W_1$ is then at least partially passed through the at least one bottoms evaporator $V_{SB}$ on the reaction column $RR_B$ and the bottoms product stream $S_{BP}$ is at least partially passed through the at least one bottoms evaporator $V_{SB}$, to transfer energy from the at least one heat transfer medium $W_1$ to the bottoms product stream $S_{BP}$.

11. The process according to claim 10, wherein the at least one heat transfer medium $W_1$ is water.

12. The process according to claim 1, wherein the vapour stream $S_{B4}$ is used for heating the rectification column $RD_A$ and/or is recycled into the rectification column $RD_A$.

13. The process according to claim 1, wherein said process is performed continuously.

14. The process according to claim 10, wherein (a2) is performed, and wherein the at least one heat transfer medium $W_1$ is at least partially passed through the at least one bottoms evaporator $V_{SA}$ and the at least one bottoms evaporator $V_{SB}$.

* * * * *

UNITED STATES PATENT AND TRADEMARK OFFICE
CERTIFICATE OF CORRECTION

PATENT NO. : 11,634,372 B2
APPLICATION NO. : 17/759116
DATED : April 25, 2023
INVENTOR(S) : Dirk Roettger et al.

It is certified that error appears in the above-identified patent and that said Letters Patent is hereby corrected as shown below:

On the Title Page

Column 2, Lines 2-3 in OTHER PUBLICATIONS currently reads:
"vol. 29,"
And should read:
--vol. 49,--;

Page 2, Column 2, Line 12 in OTHER PUBLICATIONS currently reads:
"U.S. Pat. 7,847,133"
And should read:
--U.S. Pat. No. 7,847,133--;

In the Claims

Column 24, Line 60, Claim 1, currently reads:
"the reaction column $RR_B$ and"
And should read:
--the reaction column $RR_B$, and--;

Column 25, Line 28, Claim 3, currently reads:
"consisting of and ROH."
And should read:
--consisting of water and ROH.--; and Column 25, Line 44, Claim 6, currently reads:
"wherein in step (d),"
And should read:
--wherein in (d),--.

Signed and Sealed this
Twenty-ninth Day of August, 2023

Katherine Kelly Vidal
*Director of the United States Patent and Trademark Office*